US 8,652,077 B2

(12) United States Patent
Centen

(10) Patent No.: US 8,652,077 B2
(45) Date of Patent: Feb. 18, 2014

(54) SYSTEM AND METHOD FOR DETERMINING DEPTH OF CHEST COMPRESSIONS

(75) Inventor: Corey Centen, Toronto (CA)

(73) Assignee: Physio-Control, Inc., Redmond, WA (US)

( * ) Notice: Subject to any disclaimer, the term of this patent is extended or adjusted under 35 U.S.C. 154(b) by 677 days.

(21) Appl. No.: 12/718,583

(22) Filed: Mar. 5, 2010

(65) Prior Publication Data

US 2010/0228166 A1  Sep. 9, 2010

Related U.S. Application Data

(60) Provisional application No. 61/158,002, filed on Mar. 6, 2009, provisional application No. 61/235,584, filed on Aug. 20, 2009.

(51) Int. Cl.
*A61H 31/00* (2006.01)
*A61H 31/02* (2006.01)

(52) U.S. Cl.
USPC ........................................ 601/41; 324/207.17

(58) Field of Classification Search
USPC .............. 601/41; 324/207.16, 207.17, 207.24
See application file for complete search history.

(56) References Cited

U.S. PATENT DOCUMENTS

| | | | |
|---|---|---|---|
| 4,314,251 A | 2/1982 | Raab | |
| 6,062,216 A | 5/2000 | Corn | |
| 6,323,942 B1 | 11/2001 | Bamji | |
| 7,402,996 B2 | 7/2008 | Arai et al. | |
| 2004/0082888 A1 | 4/2004 | Palazzolo et al. | |
| 2004/0267325 A1* | 12/2004 | Geheb et al. | ...... 607/5 |
| 2006/0247560 A1 | 11/2006 | Halperin et al. | |
| 2007/0252586 A1 | 11/2007 | Arai et al. | |
| 2007/0276300 A1 | 11/2007 | Olson et al. | |
| 2008/0146973 A1 | 6/2008 | Lund et al. | |
| 2008/0300517 A1 | 12/2008 | Nysaether | |
| 2008/0312565 A1 | 12/2008 | Celik-Butler et al. | |
| 2010/0022904 A1 | 1/2010 | Centen | |

FOREIGN PATENT DOCUMENTS

| | | |
|---|---|---|
| EP | 1350466 | 10/2003 |
| EP | 1491175 | 12/2004 |
| EP | 1491176 | 12/2004 |
| EP | 1645841 | 4/2006 |
| EP | 1859770 | 11/2007 |
| WO | WO03101537 | 12/2003 |
| WO | WO2004073797 | 9/2004 |
| WO | 2010009531 | 1/2010 |
| WO | 2010099628 | 9/2010 |

OTHER PUBLICATIONS

International Search Report dated Jul. 2, 2010 corresponding to International Application No. PCT/CA2010/000330.

(Continued)

*Primary Examiner* — Nicholas Lucchesi
*Assistant Examiner* — Leah Stohr
(74) *Attorney, Agent, or Firm* — Marger Johnson & McCollom PC

(57) ABSTRACT

Systems and methods for determining depth of compressions of a chest of a patient receiving chest compressions. A field detector is used having at least two coils at a fixed distance from each other.

33 Claims, 32 Drawing Sheets

(56) References Cited

OTHER PUBLICATIONS

"Compression feedback devices over estimate chest compression depth when performed on a bed," Study, Resuscitation, Jan. 2009; 80(1):79-82, Epub Oct. 25, 2008.

"Does use of the CPREzy involve more work than CPR without feedback?" study Resuscitation, Jul. 2008; 78(a):66-70. Epub, Apr. 18, 2008.

International Search Report dated Jul. 2, 2010 corresponding to International Application No. PCT/CA2010/000330, 2 pages.

* cited by examiner

SYSTEM AND METHOD FOR DETERMINING DEPTH OF CHEST COMPRESSIONS

CROSS-REFERENCE TO RELATED APPLICATIONS

This disclosure claims priority from U.S. Provisional Application No. 61/158,002, filed Mar. 6, 2009, and U.S. Provisional Application No. 61/235,584, filed Aug. 20, 2009, the disclosures of which are hereby incorporated by reference in its entirety.

TECHNICAL FIELD

This disclosure relates to systems and methods for determining depth of chest compressions, for example during the administration of cardiopulmonary resuscitation (CPR). In particular, this disclosure relates to determination of chest compression depth by use of a position sensor and a reference sensor.

BACKGROUND

There are currently an estimated 40,000 incidences of cardiac arrest every year in Canada, most of which take place outside of hospital settings. The odds of an out-of-hospital cardiac arrest currently stand at approximately 5%. In the U.S., there are about 164,600 such instances each year, or about 0.55 per 1000 population. It may be desirable to decrease the number of deaths resulting from these out-of-hospital incidences of cardiac arrest. Certain places, such as sports arenas, and certain individuals, such as the elderly, are at particular risk and in these places and for these people, a convenient solution may be the difference between survival and death.

Cardiopulmonary resuscitation (CPR) is a proven effective technique for medical and non-medical professionals to improve the chance of survival for patients experiencing cardiac failure. CPR forces blood through the circulatory system until professional medical help arrives, thereby maintaining oxygen distribution throughout the patient's body. However, the quality of CPR is often poor. Retention of proper CPR technique and protocol may be inadequate in most individuals and the anxiety of an emergency situation may confuse and hinder an individual in delivering proper treatment.

According to the Journal of the American Medical Association (2005), cardiopulmonary resuscitation (CPR) is often performed inconsistently and inefficiently, resulting in preventable deaths. Months after the completion of standard CPR training and testing, an individual's competency at performing effective chest compressions often deteriorates significantly. This finding was found to hold true for untrained performers as well as trained professionals such as paramedics, nurses, and even physicians.

The International Liaison Committee on Resuscitation in 2005 described an effective method of administering CPR and the parameters associated with an effective technique. Parameters include chest compression rate and chest compression depth. Chest compression rate is defined as the number of compressions delivered per minute. Chest compression depth is defined as how far the patient's sternum is displaced by each compression. An effective compression rate may be 100 chest compressions per minute at a compression depth of about 45 cm. According to a 2005 study of actual CPR administration at Ulleval University Hospital in Norway, on average, compression rates were less than 90 compressions per minute and compression depth was too shallow for 37% of compressions.

Therefore, a system to facilitate the proper delivery of CPR in an emergency may be useful. Furthermore, a system that can also be used in objectively training and testing an individual may be useful for the CPR training process and protocol retention.

Most existing CPR assist technologies use accelerometers for the determination of compression depth. One such device is disclosed in U.S. Pat. No. 7,074,199. However, any acceleration data from accelerometers used to measure the depth of chest compression during CPR is prone to cumulative errors and drift errors. Consequently, these sensors are not suitable for highly accurate or detailed data collection regarding CPR parameters and can only be relied on for approximate depth values. Furthermore, the use of an accelerometer in a CPR monitoring device without an external reference is prone to error if the patient or CPR administrator is mobile. For example, if the patient is being medically transported in an ambulance, helicopter or on a gurney, the accelerometer is unable to differentiate between the external movement of the patient and the compressions of the chest. In any type of non-stationary environment, an accelerometer based device may be unreliable and ineffective. The use of an accelerometer to calculate compression depth also relies on complicated and error-prone calculations to compensate for the angle and tilt of the compression device. If the accelerometer is not perfectly level on the chest of the patient and its movement is not perfectly vertical, errors may accumulate and must be accounted for by the angle of the two horizontal axes. Furthermore, the absence of any external reference point makes it difficult for the device to know its position in space at any given time. All measurements of distance are relative and an origin of movement is difficult to ascertain and maintain over the course of measurements. This may cause the initiation or starting point of the compressions to drift over time leading to errors in depth measurements. Certain commercial products currently use accelerometer technology, such as the AED Plus® D-Padz® from Zoll Medical, in which the accelerometer is embedded into the pads of the defibrillator. Due to the additional circuitry and sensory within them, these defibrillator pads are substantially more expensive and must be disposed of after each use. Therefore, relatively expensive sensory must be routinely discarded due to the design of the product.

U.S. Patent Application Publication No. 2007/0276300 to Kenneth F. Olson et al. discloses a device using ultrasound transmission to calculate compression depth. An acoustic signal is transmitted from a device on the chest of the patient to a receiver in another location. This device has several drawbacks. First, the ultrasound signal must have a clear line of sight from transmitter to receiver in order to operate. Any interference, objects, people or even the hand of the user in the way of the signal may result in signal loss or deterioration. The transmitter must be directed toward the receiver and the relative orientation between the transmitter and receiver is crucial. Second, ultrasound is relatively slow and a time-of-flight measurement of an ultrasound signal may suffer from significant lag and latency. Third, an ultrasound signal is highly dependent on ambient conditions such as air temperature. If air temperature fluctuates, so does the speed of sound, which may result in inaccuracies. Finally, if the plane of the chest compression is initially unknown, the calculation of compression depth may be significantly compromised. Time-of-flight ultrasonic distance interpolation cannot resolve the position of the receiver in six degrees of freedom and the determination of the downward translational movement if the patient, receiver or transmitter is not level may be difficult. Even if ultrasonic triangulation is employed, latency may be significant, resolution may be low and multiple transmitters and receivers in different locations may be required.

Existing CPR assist devices and systems are relatively ineffective at measuring chest recoil. Chest recoil is the extent to which the chest is released following a compression. For a chest compression to be completely effective, the chest must be fully released before beginning another compression. When a compression is released, elastic recoil will create a negative pressure that pulls blood into the chest. Incomplete decompression will reduce the amount of blood available to be circulated with the next compression. Accelerometer-based devices lack the ability to establish a reference point at the top of a compression that may be used to adequately measure recoil. As there is no external reference, the accelerometer signal may drift over time and the device may become ineffective at determining whether the chest has been fully released.

A recent study (Resuscitation. 2009 January; 80(1):79-82. Epub 2008 Oct. 25: 'Compression feedback devices over estimate chest compression depth when performed on a bed') has unearthed another inadequacy in current CPR assist devices. The study indicates that CPR assist devices tend to overestimate compression depth when the patient is on a mattress. The device tends to erroneously register the movement of the mattress as part of the chest compression.

Other CPR assist tools use mechanical force measurements as an indication of compression depth. These devices may be inaccurate due to their inability to compensate for varying chest compliances. They tend to rely on the user's subjective impression of the patient's body size to help calibrate the proper amount of force to be administered. Furthermore, a recent study (Resuscitation. 2008 July; 78(1):66-70. Epub 2008 Apr. 18: 'Does use of the CPREzy involve more work than CPR without feedback?') has shown that these devices tend to require more work than CPR without an assist tool due to the device's internal mechanism. The spring within the device may add an additional 20% workload to the CPR process leading to a faster onset of user fatigue.

Presently available CPR assist devices and system typically suffer from a major disadvantage. They tend to indirectly measure depth by first determining acceleration, velocity or force. Ultimately compression depth is a measure of position and the determination of acceleration requires doubly integrating the received signal to obtain useful data. Such integration introduces a significant source of error into the measurement. It may be desirable to provide a method of determining CPR compression depth by measuring position, rather than acceleration, velocity or force. By measuring position directly, errors related to integration of the signal or compliance of the patient's chest are not introduced. The position data may be used to directly calculate the depth of chest compressions.

It may be desirable to provide an easy-to-use and inexpensive system to accurately measure relevant CPR parameters such as compression depth and rate absent of the problems in the aforementioned technologies.

SUMMARY

The present disclosure is directed to a method and system for determination of compression parameters during administration of CPR. The system includes the features and methods disclosed in patent applications Nos. 61/158,002 and 61/235,584, and provides additional processing strategies and hardware components. The aforementioned applications describe the use of a field generator and a field detector. The generator and detector may be used as a reference sensor and a position sensor. The reference sensor is relatively stationary, while the position sensor is placed on the patient's chest and moves according to each chest compression. The field generator and field detector specifically generates and detects a field, such as an electromagnetic field, rather than simply transmitting and receiving a signal.

In some aspects, there is provided a compound field detector for determining a depth of compression of a chest of a patient receiving chest compressions, the detector comprising: at least two coils at a fixed distance from each other; wherein the detector is adapted to generate a response signal indicative of any one of the at least two coils detecting a field.

In some aspects, there is provided a method for determining a depth of compression of a chest of a patient receiving chest compressions, the method comprising: determining the positions of at least two coils adapted to move in accordance with the chest; estimating an apparent distance between the coils; estimating a correction factor based on any differences between the apparent distance and a known distance between the coils; and determining the chest compression depth based on the determined positions and the correction factor.

In some aspects, there is provided a system for determining a depth of compression of a chest of a patient receiving chest compressions, the system comprising: a field generator adapted to generate a field; a compound field detector including at least two coils at a fixed distance from each other, the field detector adapted to generate a response signal indicative of any one of the at least two coils detecting the field; and a processor adapted to determine from the response signal position information for the field detector relative to the field generator, and to determine the chest compression depth from the determined position information; wherein one of the field generator and the field detector is a position sensor adapted to move in accordance the chest as the chest is receiving the compressions, and the other of the field generator and the field detector is a reference sensor adapted to be stationary relative to the patient.

Due to the relatively uniform and predictable nature of chest compressions, various computational algorithms may be used to relatively accurately calculate CPR parameters. Expected sources of error such as signal jitter and distortion caused by highly ferrous and conductive metals may be reduced or eliminated through the implementation of equations and/or filtering techniques tailored to the properties of chest compressions.

Beyond computational algorithms, other techniques may be employed to reduce or eliminate error, noise and/or distortion in the measured CPR parameters. As in software, the unique properties associated with the movement of a chest compression may enable unique hardware designs that result in cleaner, more reliable position and/or depth estimates. Specifically, the field generator and field detector coils may be configured to reduce the effects of metallic disturbances in the operational environment. In some examples, a compound detector may be used in which two or more detectors in a fixed relationship are used together. The known separation distance between the centers of these two or more detectors may be used to detect and compensate for distortion in the environment (e.g., due to metallic objects). In some examples, the addition of a second sensing modality may assist in further reducing error by detecting the presence of distorted or otherwise incorrect data. For example, a pressure or force sensor may detect errors originating from sources that do not affect the pressure or force sensor but do affect the field coils (e.g., distortion from metallic objects).

In some aspects, there are provided methods that may be employed to compensate or correct for potential sources of system error or failure resulting from external perturbations of the system. For example, if the reference sensor is moved during the administration of CPR, the system may detect such a movement and recalibrate the depth calculation accordingly to compensate for the movement. In some examples, the system may continue to operate during this disturbance. The continuous operation during movement of the reference sensor may be accomplished through the addition of an external sensor unaffected by the movement, such as a force or pressure sensor.

In some aspects, there are also provided methods for the compensation of unsatisfactory or error-prone environments in which the system may be operated. For example, the system may be configured to compensate for a situation in which the patient is supported on a non-rigid surface, such as a mattress. A non-rigid surface may exhibit motion or displacement during administration of CPR, which may result in erroneous measurements if not taken into account. For example, during CPR, the mattress below the patient is compressed along with the chest. This may result in an erroneously large compression depth measurement that is not indicative of the actual depth that only the chest, in the absence of the mattress, is compressed. The use of an additional field detector may overcome this problem. Given the three components of a first detector, a second detector and a generator, one component may be adapted to move in accordance with the non-rigid surface (e.g., placed on the mattress below the patient), a second component may be adapted to move in accordance with the patient's chest (e.g., placed on the patient's chest), and the third component may be adapted to be stationary relative to the patient. The actual depth of compressions may then be determined by determining the relative motion between the component (e.g., the first detector) moving with the non-rigid surface and the component (e.g., the second detector) moving with the patient's chest, for example by subtracting the position of one from the position of the other.

In some examples, depending on the specific situation, the system may be adaptable to the emergency. For example, the position sensor may be removably housed in a sheath or housing. The sheath may protect the user's hands while providing additional comfort. In some examples, the sheath may be removed from the position sensor when the system is used to perform CPR on an infant. The removal of the sheath may transform the position sensor from an adult-sized pad to an infant-sized pad. In some examples, the position sensor may also be affixed or housed in a number of items found at an emergency scene. For example, one or both of the generator and detector may be affixed to a patient backboard, embedded within the electrodes of a defibrillator or attached to a gurney or a hospital bed.

BRIEF DESCRIPTION OF THE DRAWINGS

Aspects of the present disclosure will be discussed in detail below, with reference to the drawings in which.

DETAILED DESCRIPTION

The present disclosure is directed to a method and system for the determination and calculation of chest compression parameters, such as chest compression depth, during the administration of cardiopulmonary resuscitation (CPR). The system may also be referred to as a CPR assist system.

The system includes a field generator and a field detector. In some embodiments, the field detector is a position sensor and the field generator is a reference sensor. The position sensor may be placed at a location that corresponds to movement of the patient's chest, while the reference sensor may be placed at a relatively stationary location. Signals, for example electromagnetic fields, are generated by the reference sensor and detected by the position sensor. In other embodiments, the field detector is the reference sensor and the field generator is the position sensor, in which case signals, which may be fields, are generated by the position sensor and detected by the reference sensor. It would be clear to a skilled person that the position sensor and reference sensor are interchangeable. A processor in the system determines the position of the position sensor relative to the reference sensor based on the signal. Based on the determined position, the processor determines the chest compression parameters, including chest compression depth, during administration of CPR.

Figure 1:
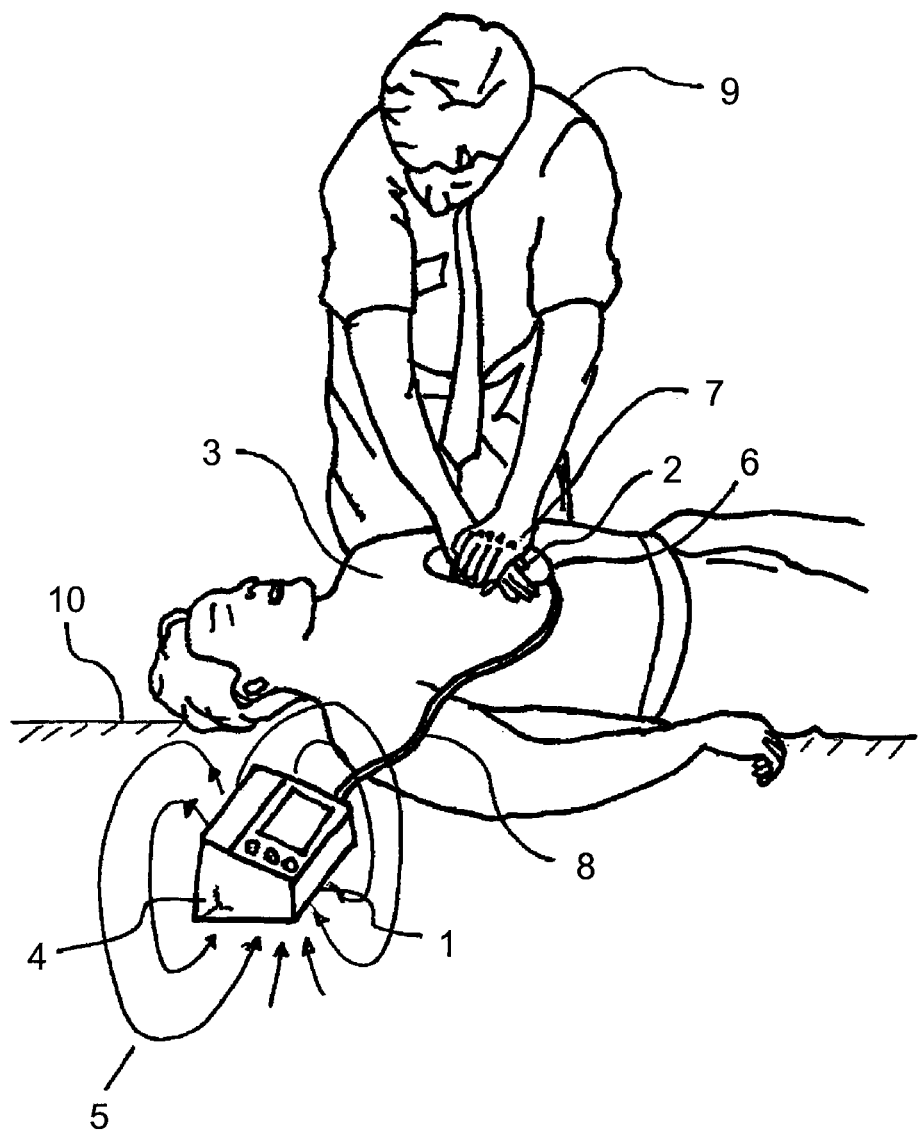
FIG. 1 is an illustration of a CPR assist system in accordance with an embodiment of the present disclosure.
Figure 2:
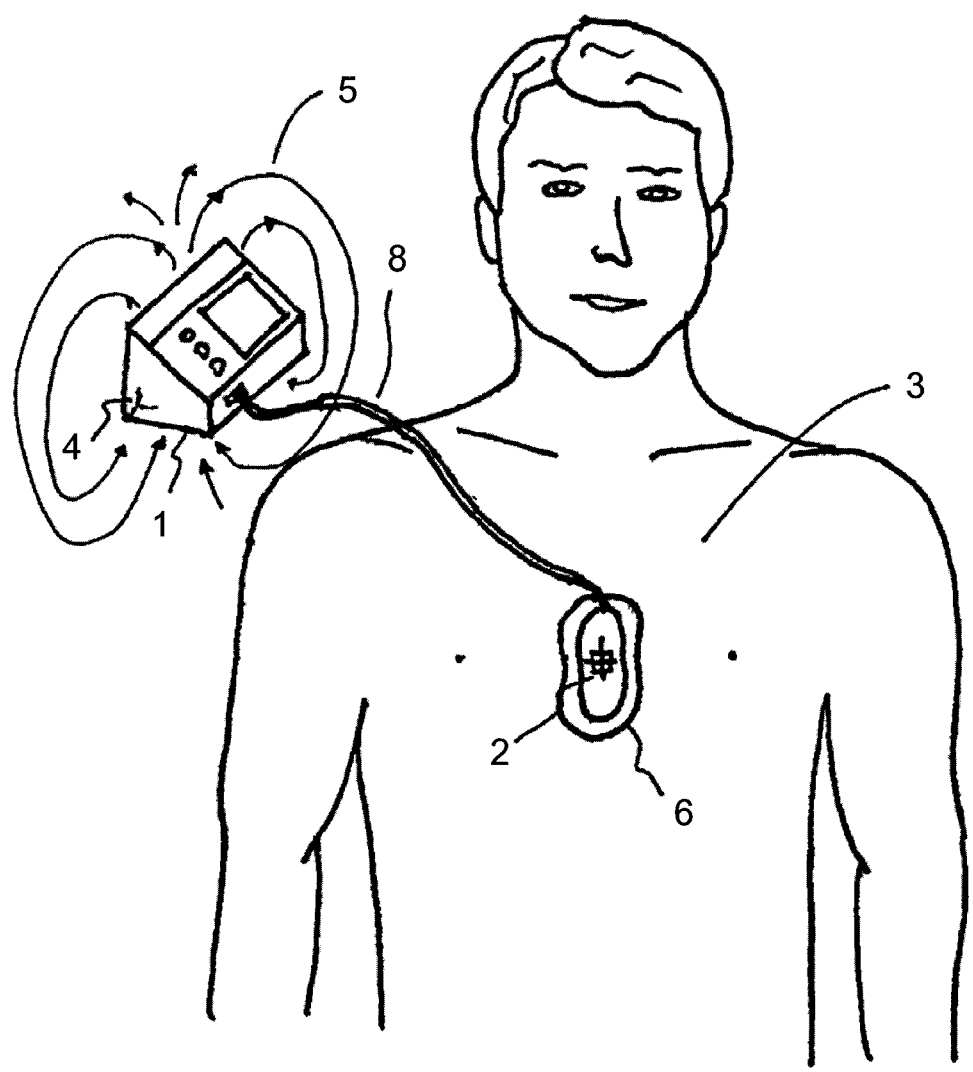
FIG. 2 is a top plan view showing a field detector of a CPR assist system within a pad on the patient's chest.

Reference is now made to FIGS. 1 and 2. In this example, the CPR assist system may include a relatively stationary base unit 1 containing a reference sensor 4 in the environment of an emergency and a position sensor 2 that may move according to a patient's chest movement, relative to the reference sensor 4, thus tracking the movement of the chest of the patient 3 during CPR. In this example, the reference sensor 4 is the field generator and the position sensor 2 is the field detector. The reference sensor 4 is capable of generating a signal, such as a field 5, that is detected by the position sensor 2. In this example, the position sensor 2 is provided in a structure placed on the chest of the patient, such as a block, pad 6 or other suitable structure and is connected to the base unit 1 by a cable 8. The CPR administrator or user 9 may compress the chest of the patient directly by placing his or her hands 7 on the pad 6. Here, the base unit 1 is placed on the ground 10, which is relatively stationary relative to the patient. Although the base unit 1 is shown, in some examples the system does not include a base unit.

Figure 3:
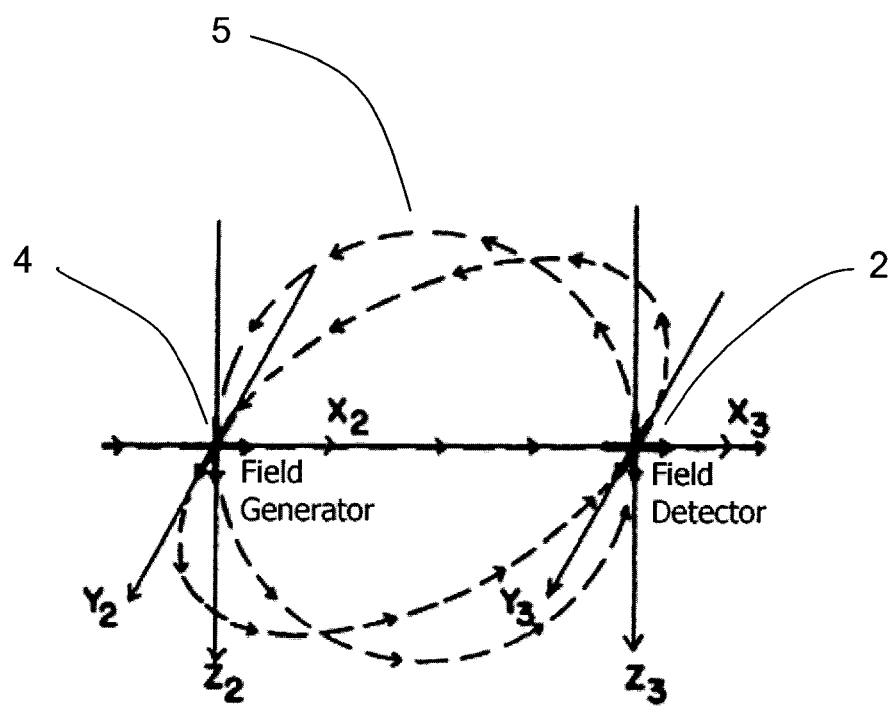
FIG. 3 is an illustration of a field generated by an example field generator and detectable by an example field detector suitable for an example embodiment of the CPR assist system.

As shown in FIG. 3, the field detector (e.g., the position sensor in the above example) is configured to sense the generated field from the field generator (e.g., the reference sensor in the above example). The field detector may then produce a response signal. A processor determines the position of the position sensor, for example its three-dimensional position coordinates, relative to the reference sensor, based on the response signal. The processor may be provided together with the reference sensor in the base unit, may be provided on the position sensor, or may be a separate component. The processor may receive information from the position sensor through wired or wireless communication. For example, the position sensor may include a wire for coupling with the reference sensor and/or the processor, or may include a wireless transmission component for wireless coupling with the reference sensor and/or the process. Similarly, the reference sensor may communicate with the processor through wired or wireless communication.

The determination of the position sensor's coordinates may be accomplished by measuring the strength of the field detected from the field generator. The position information may be used by the processor to determine a chest compression parameter, such as chest compression depth. The chest compression parameter (e.g., chest compression depth) may be provided to the user through a feedback component, for example through audible, visual and/or tactile feedback. Chest compression depth may be determined from the position information by determining initial and final positions corresponding to the start and end of a single compression and subtracting one from the other. Other common calculations may be used for determination of chest compression depth.

Possible hardware and software that may be used to calculate three degree of freedom coordinate position information is disclosed in U.S. patent application Ser. No. 12/354,913, the disclosure of which is hereby incorporated in its entirety by reference. That application discloses methods of demodulating and filtering the response signal to generate a 3×3 signal matrix representative of the nine generator-detector couplings. Calculating position may be accomplished using methods similar to those disclosed in U.S. Pat. No. 4,314,251, the disclosure of which is hereby incorporated in its entirety by reference. One method of calculating position uses a three-axis field detector. The three-axis sensor determines the complete signal vector produced at the position sensor location by each excitation vector of the field generator. Orientation of the position sensor relative to the reference sensor is initially unknown and position may, therefore, be determined from signal parameters that are unaffected by sensor orientation unknowns. Solutions for the unknown position of the sensor may be formulated in terms of squared magnitudes and the dot products of sensor output vectors. Both of these quantities are invariant under sensor rotation.

For example, the magnitudes of the three coordinates of the position of the sensor may be determined through a system of equations based upon the outputs of a three-axis position sensor produced by all three excitation vectors. Trigonometric relationships and position-frame sensor-output vectors corresponding to the excitation vectors may be used to determine relationships between the squared vector magnitudes and the x, y and z coordinates.

Figure 4:
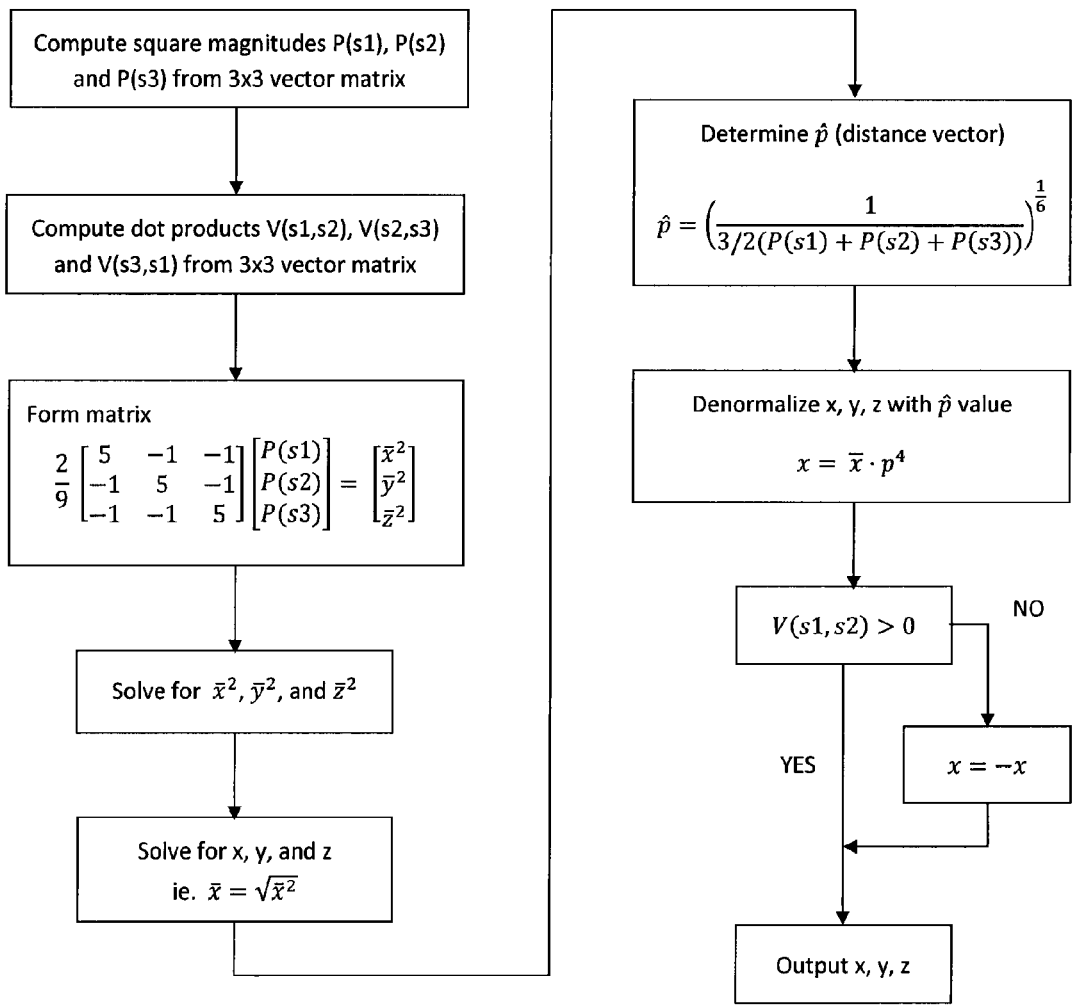
FIG. 4 is a flowchart showing an example algorithm for the calculation of position.

Once the x, y, and z values are determined, the coordinates may be denormalized if appropriate. The signs of the x, y and z coordinates are determined by the dot products of the sensor output vectors. The process for calculating x, y and z may be modified for sensors and sources of fewer or greater than three axes. One example method of calculating the position of the position sensor is shown in FIG. 4.

Figure 5:
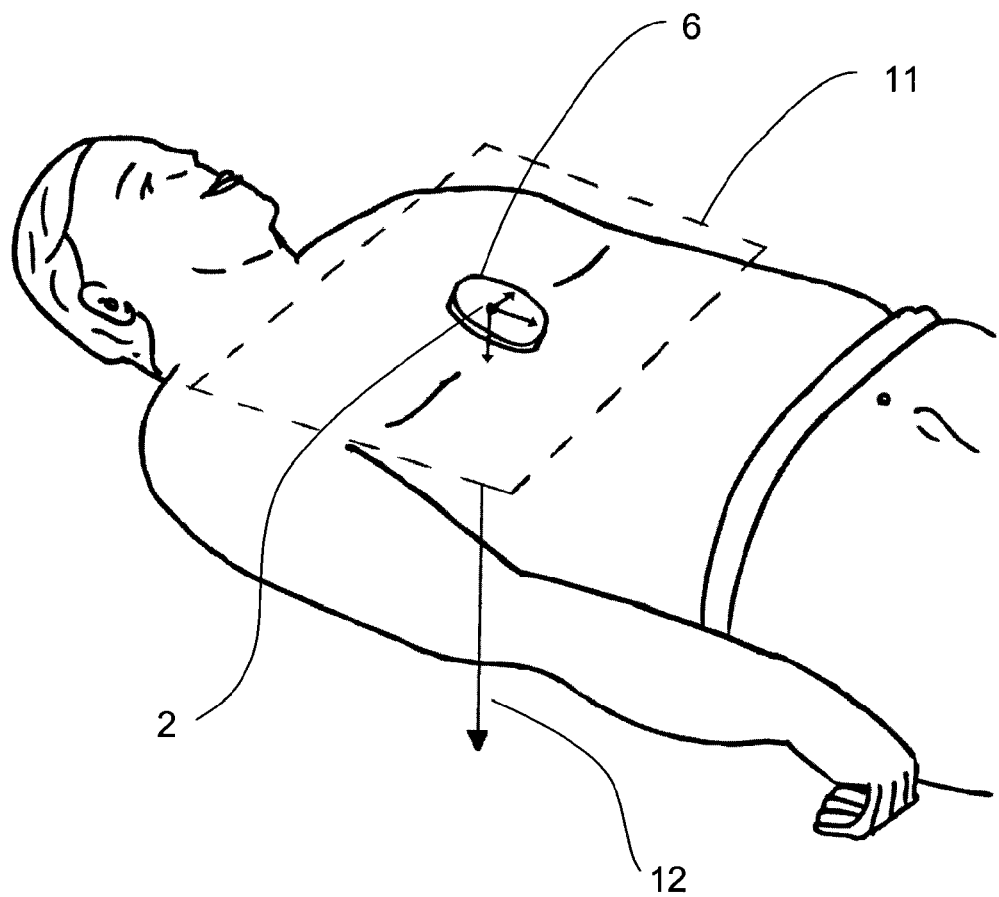
FIG. 5 is an illustration showing an example method of calculating chest compression depth by first forming a plane in space.
Figure 6:
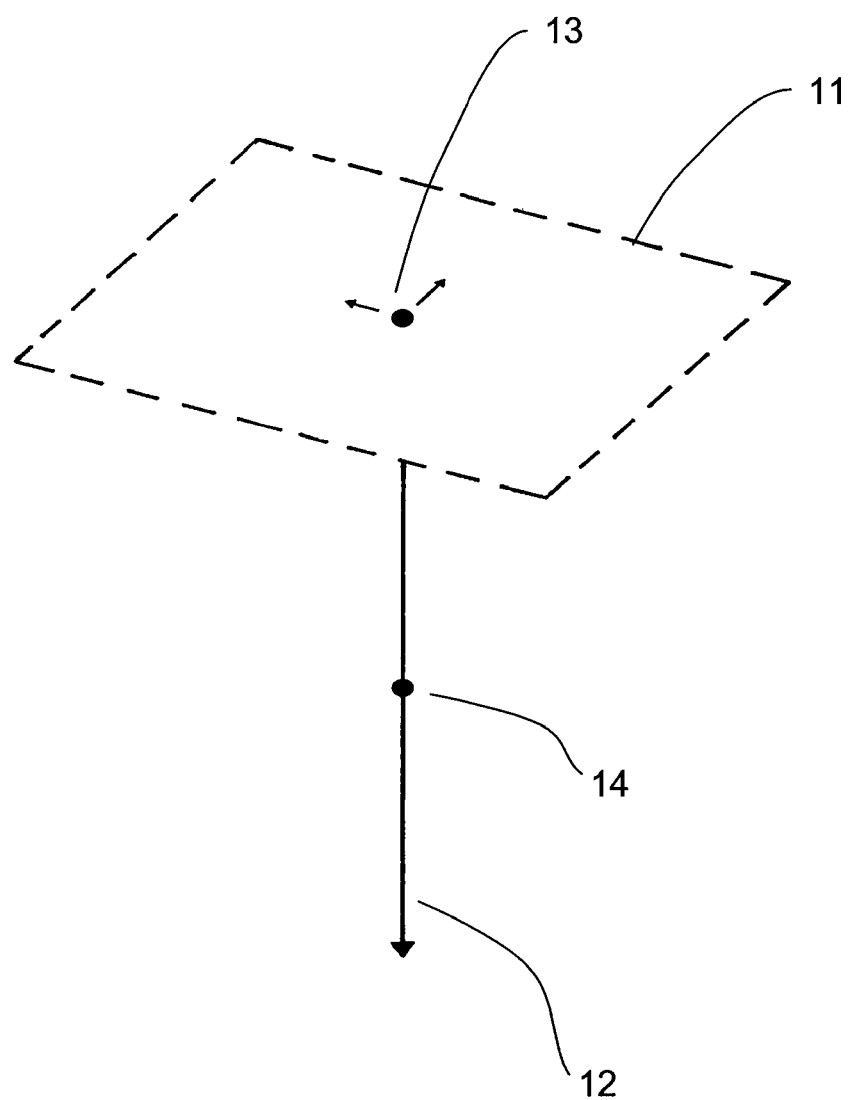
FIG. 6 is a diagram showing a normal vector parallel to the path of a chest compression and its corresponding plane in space.
Figure 7:
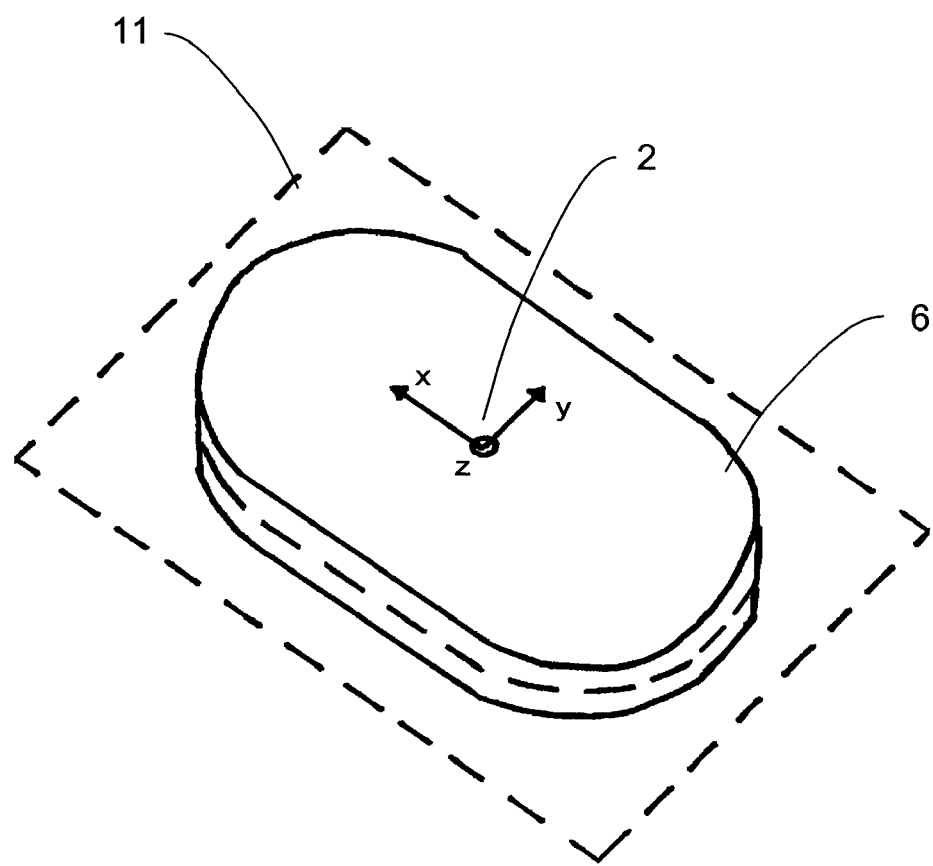
FIG. 7 is an illustration showing an example pad housing an example position sensor and the plane bisecting the pad.

Upon obtaining x, y and z coordinates for the position of the sensor, the calculation of compression depth and other parameters may be performed. A number of methods may be used to calculate chest compression depth. For example, where the field generator provides the reference frame for the system, the calculation of chest compression depth may be accomplished by forming an imaginary plane 11 in space that is substantially parallel to the patient's chest as shown in FIG. 5. This plane 11 forms a reference location for the start of a chest compression and the chest compression depth is calculated as a distance from the plane. The equation of the plane may be calculated by forming an initial vector 12 along the downward motion of the first compression. A starting, reference or "home" coordinate 13 and one or more other coordinates 14 along the length of the compression may determined and stored in memory as shown in FIG. 6. The normal vector 12 for the plane may be calculated using these coordinates. The equation of a plane is Ax+By+Cz+D=0 where (A,B,C) is the vector normal to the plane. The value of D may be calculated by substituting the "home" coordinates into the plane equation and solving. The calculated plane represents the highest depth level that the position sensor may achieve during a chest compression. For example, the plane may be substantially parallel to the patient's chest and substantially parallel to the top surface of the pad 6 housing the position sensor 2 as shown in FIG. 7. The compression depth may then be calculated as the current coordinate's distance from that plane. The distance to the plane from any current coordinates (x, y, z) is calculated as:

$$d = \frac{Ax + By + Cz + D}{\sqrt{A^2 + B^2 + C^2}}$$

The sign of d may be used to determine if the current compression coordinate is above or below the starting position of the chest compression. Any value indicating a compression position above the plane is likely to be erroneous or may represent movement of the pad that is not part of the chest compression. Adequate chest recoil may also be calculated by ensuring the user sufficiently releases the chest of the patient such that the sensor returns to the starting plane position.

Figure 8:
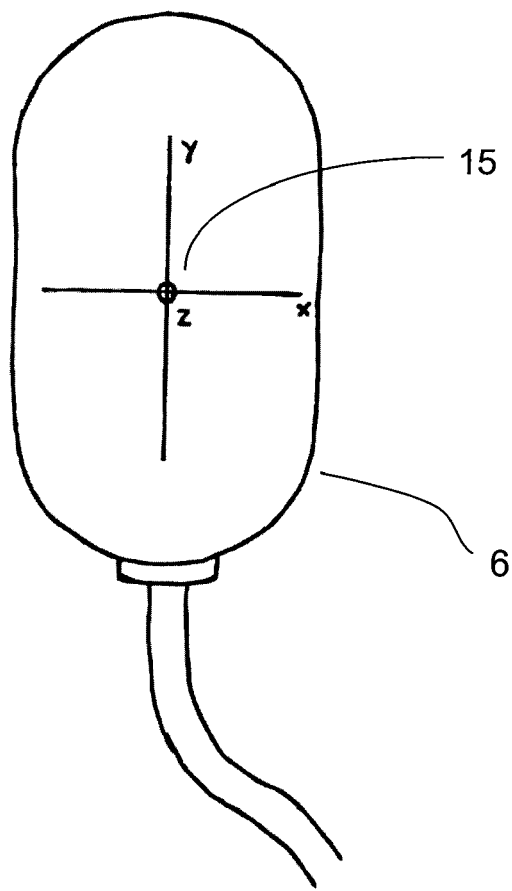
FIG. 8 is an illustration of an example pad housing an example position sensor in which the coordinate axes are labeled on the pad.

Another example method of determining the depth of a chest compression is to use the position sensor to provide the reference frame for calculations. If the position sensor is the reference frame, rotations of the reference sensor will not affect the x, y, z coordinates of the position sensor. Therefore, the initial rotation of the reference sensor may not be relevant to the current x, y, z position of the position sensor as the position sensor is moving in its own reference frame. The calculations may be moved from the reference sensor frame-of-reference to the position sensor frame-of-reference by simple rotations known to those skilled in the art. The starting configuration (i.e. orientation) of the position sensor may be known relative to the chest of the patient. For example, in a CPR assist system, the pad 6 housing the position sensor may be marked with lines 15 indicating where on the patient's chest the pad should be placed as shown in FIG. 8. The pad may be placed, for example, between the nipples of the patient and on the sternum. Since the position sensor frame-of-reference is the reference frame, all movements of the position sensor are relative to its own current position and configuration. Therefore, the coordinate positions calculated during a chest compression may be used to directly determine compression depth. The actual x, y, z trajectory of the position sensor through three dimensional space may be tracked as the compression is administered, or the distance between the starting coordinate of the compression and each current coordinate may be calculated to determine the present compression depth.

By tracking the coordinates through space, rather than calculating the distance between points directly, other algorithms may be developed that are able to account for lateral shifting of the system and/or other movements that are not part of the chest compression. For example, a sideways movement of the position sensor 2 may be misconstrued as a portion of the vertical movement of the compression. Errors resulting from these spurious movements may be reduced or eliminated by monitoring the three dimensional trajectory of the position sensor as it moves through the chest compression. Lateral, non-compression components of motion may be eliminated from the calculated depth. This may be an advantage of measuring the x, y, z position of the position sensor directly over traditional systems employing accelerometers and force sensors that cannot easily differentiate such spurious movements.

In another example method of calculating compression depth, the field generator is adapted to move in accordance with the patient's chest (e.g., in a pad placed on the chest) and the field detector is adapted to be stationary relative to the patient. Since the field generator is the reference frame for the system, all position data will be in the frame of the pad on the chest of the patient. Therefore, as above, the pad may be marked with landmarks or reference points to align the pad properly on the chest. The known configuration of the pad relative to the chest may allow the present position and depth of the chest compression to be relatively accurately monitored. Unlike in the previous method, this technique does not require rotating the coordinates into the position sensor frame as the field generator is the position sensor and all measurements are relative to the field generator.

Figure 9:
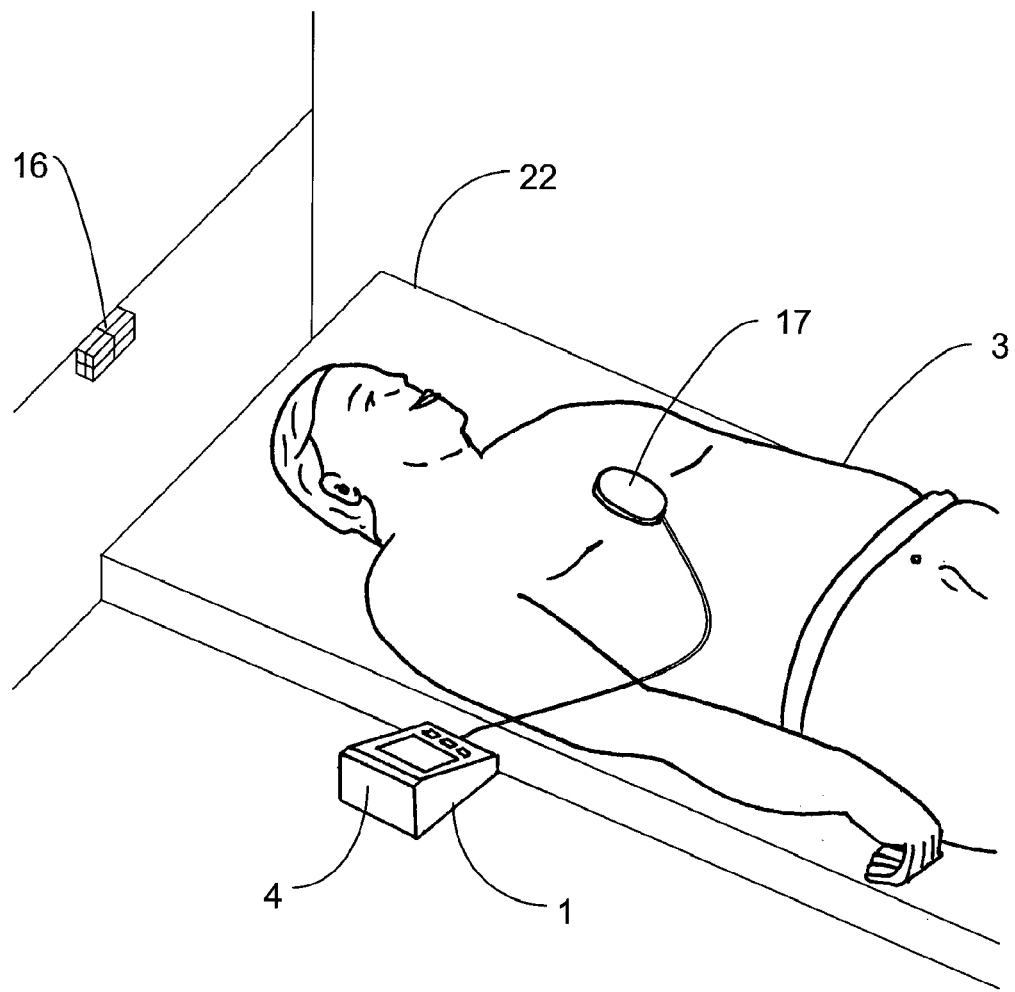
FIG. 9 is an illustration showing an example embodiment of the CPR assist system in which a second field detector is placed in a stationary position in the environment.

As described previously, either the field detector or the field generator may be used as the position sensor, and the other of the pair may be used as the reference sensor. Multiple reference and/or position sensors may be used, which may further improve the accuracy of the position and orientation information. For example, in an environment with a significant source of noise or interference (e.g., in the case where the system uses electromagnetic fields as signals, a noisy environment may be one containing significant sources of metal), a second field detector 16 may be placed in the environment of the first field detector 17, where the first field detector is used as a position sensor and the reference sensor is a field generator as shown in FIG. 9. This second field detector may be relatively fixed in position and used to calibrate the measurements of the system by determining the ambient interference in the environment. For example, within an ambulance, an existing field detector may be fixed within the environment and may be able to measure the ambient distortion present within that environment.

Electromagnetic tracking systems, such as the one described in U.S. Pat. No. 4,313,251, the disclosure of which is hereby incorporated in its entirety by reference, may suffer from a major limitation. The electromagnetic signals generated by these systems are typically prone to distortion caused by the presence of metallic objects. The major sources of distortion are primarily large, conductive metallic objects. There are two properties of a metal that determine the extent to which it will distort an electromagnetic field. The first property is the conductivity of the metal. Varying fields, such as sinusoidal electromagnetic fields, generate eddy currents in conductive materials. The extent to which eddy currents are produced is dependent on the size and conductivity of the material. Very conductive metals, such as copper, are more threatening to the field than less conductive metals such as stainless steel. The second property is the permeability of the metal. Materials that are highly permeable at the frequency of the generated field may skew the detected field.

Cautionary steps may be taken with current electromagnetic tracking systems to reduce metallic interference. For example, the distance between the field generator or field detector and any large metallic object may be increased until the effect is negligible. Alternatively, the separation distance between the field generator and field detector may be minimized thereby reducing the distortion caused by any nearby metal. It is also possible to map out all the sources of metal in the environment prior to collecting data. However, these and other existing methods of distortion compensation may not be practical in a number of operating situations. For example, in a real-world environment, it is often difficult and cumbersome to ensure all sources of metal are completely removed. It is also often difficult and time consuming to locate and map each and every metallic source prior to operation of the system. In applications where metal may be present, but fast and reliable operation is required, mapping is often not a practical option.

Certain tracking applications require only relative measurements of position and involve a relatively predictable trajectory of motion. For example, the application may require tracking over a simple, linear path such as the path traveled by the chest of a patient during the administration of CPR. During CPR, the vector along which the chest will travel is substantially known (i.e. the chest will be compressed toward the spine along a substantially straight, downward path). The properties of this linear motion along a substantially known vector may be used to improve the accuracy of the data while reducing or eliminating distortion from metallic noise and/or interference from other electrical devices.

Figure 10:
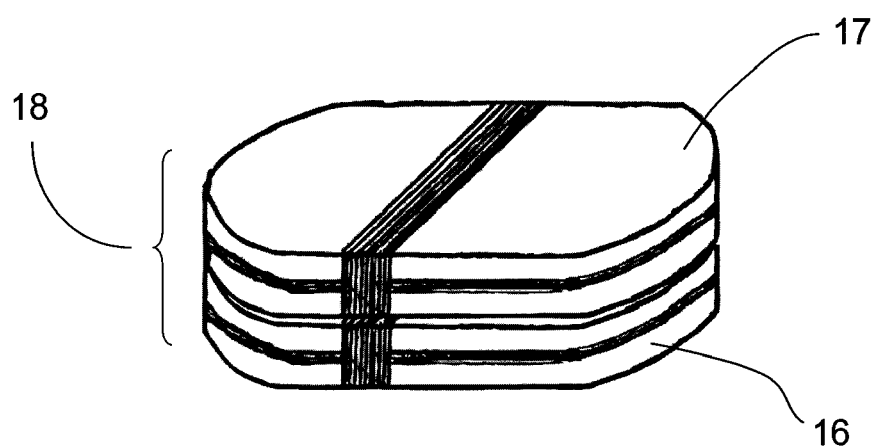
FIG. 10 is an illustration showing two example position sensors placed in fixed relation to each other, in a compound detector.
Figure 11:
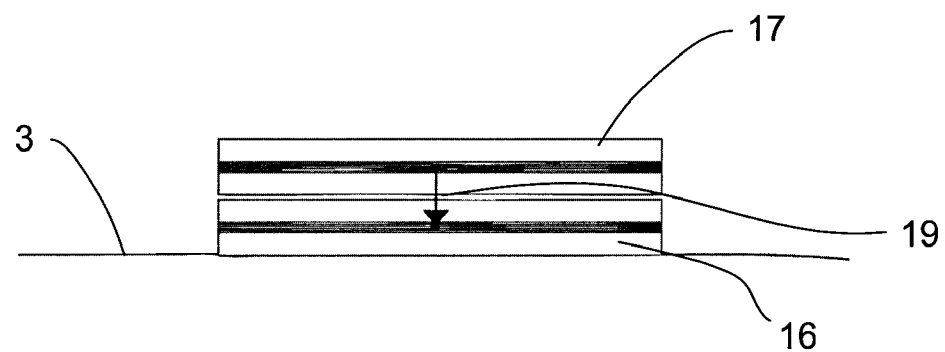
FIG. 11 is a diagram showing the normal vector joining the centres of the position sensors in the configuration of FIG. 10.

For example, reducing the effects of metallic distortion while improving accuracy in an electromagnetic system where the object to be tracked moves along a known vector path (such as in CPR), may be accomplished through the use of a compound detector having at least two coils in a fixed distance from each other. The compound detector behaves similarly to a simple (i.e., non-compound) detector, however response signals from the compound detector may be generated by either one or both of the coils. For example, a second field detector 16 may be affixed directly below the first field detector 17, both moving together as one unit, also referred to as a "stacked detector" or compound detector 18, as shown in FIG. 10. In the example compound detector 18, there are at least two coil assemblies (in this case, field detectors 16, 17) having windings substantially parallel to each other and spaced apart from each other at a fixed and known distance. Although the compound detector 18 is described as having two or more detectors, it should be understood that the compound detector 18 may have two or more spaced apart coils or coil assemblies rather than detectors. The known spacing is in a direction substantially parallel to the direction of expected motion (in this case, perpendicular to the parallel windings). In the example shown, the two detectors 16, 17 may be placed directly on top of each other so that corresponding coils are parallel to each other and so that the centre of one detector 16 is directly above the center of the other detector 17. A longitudinal axis 19 that is perpendicular to the planes defined by each of the windings and connecting the centres of each field detector 16, 17 may run substantially directly along or parallel to the expected path of the motion (i.e. path of chest compression) to be measured as shown in FIG. 11. Because the two detectors 16, 17 are stacked and fixed together, the distance between the centres of the two field detectors 16, 17 is a known and fixed constant value.

The raw data from each of the two field detectors in the compound detector 18 may be correlated to obtain more accurate position information. The known separation distance may be used to detect sources of distortion and/or noise in the environment, and used to correct for the distortion and/or other sources of noise. Although two field detectors are shown in the compound detector, more than two field detectors may be used, provided the distances among the field detectors are all known and fixed. Where there are more than two detectors in the compound detector, the field detectors may all be distanced from each other along the same direction (e.g., parallel to the expected direction of compression) or along different directions. Where the field detectors are distanced from each other in different directions, such a configuration may be useful for determining and correcting for distortions in multiple directions.

There are a number of ways in which the coils within the compound detector may be used to compensate for metallic objects present in the environment. For example, when a conductive or ferrous metal is close to the detector or generator, the measured absolute position from the source to each of the field detectors will be distorted. The distortion will cause the known and fixed distance between the two field detectors be detected as being apparently closer lesser or greater, depending on the type of distortion present. This discrepancy between the known actual fixed distance and the measured apparent distance is an indicator of the type and magnitude of distortion present along the path of motion. This information may be used to calculate the effect of the distortion on the detector as it moves through a motion along the vector joining the centers of the detector coils. As the vector joining the two detector's centres is substantially aligned or parallel with the axis of the motion, the distortion along that vector and hence, along the length of the motion may be determined.

For example, if the actual distance between the detector coils in the compound detector configuration is five millimetres and the measured apparent distance is ten millimetres, a scaling factor of two may be used on the motion measured over the distance separating the coil. Therefore, if the detector has a measured apparent movement of four millimetres, its actual movement may be corrected to be actually two millimetres. Although the distortion may not cause a linear effect over the vector path separating the detectors, the approximation may nonetheless help to improve the position estimate. Other such correction factors may be used. For example, scaling or correction factors may be collected over a period of time or a number of compressions and aggregated (e.g., averaged together) to correct any measurement distortions.

Figure 12:
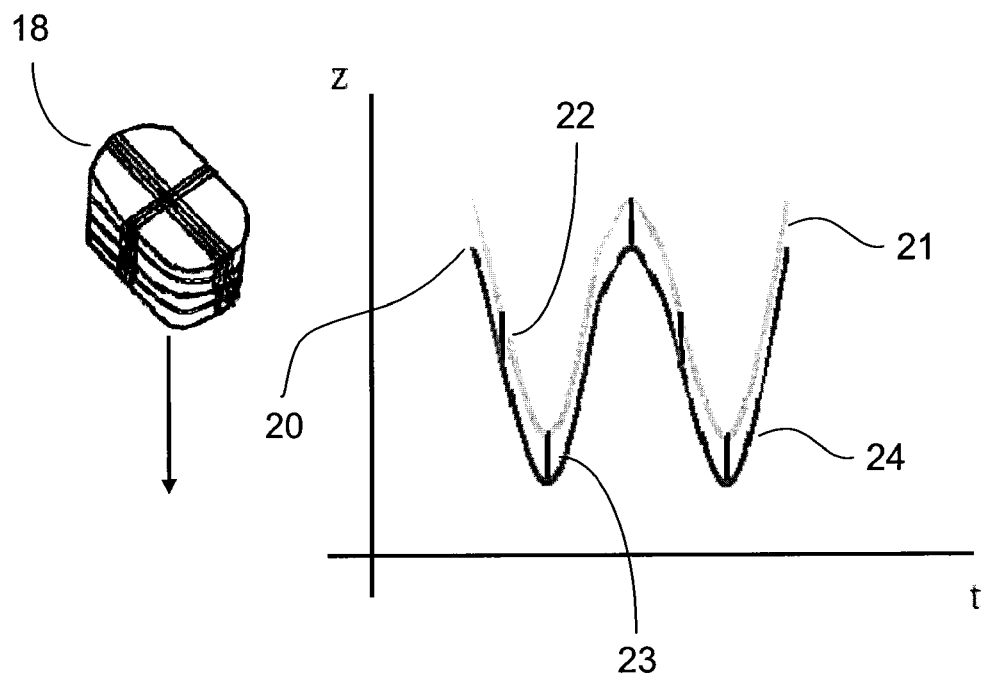
FIG. 12. is an illustration showing the movement of each field detector in the configuration of FIG. 10.

Another example approach to distortion compensation using the compound detector may be to map out a new coordinate system along the path of motion. As long as the movement of the detector occurs substantially along or parallel to the path joining the detectors and the separation distance between the detectors is sufficiently small, one of the two detectors will move through the initial position of the other. When the position of the first detector moves into the position previously occupied by the second detector, the measured coordinates of the first detector should be equal to or very similar to the coordinates of the second detector when it was in the same position. Even if a metal distorter is present in the environment, the coordinates of the first detector will be distorted in the same way the coordinates of the second detector were distorted in that same position. Therefore, the second detector may map out a new distorted coordinate frame for the first detector along the path of travel as shown in FIG. 12.

For example, if the position of the chest is being measured during the administration of CPR, the compound detector may be positioned on the chest of the patient such that the vector joining the centers of the detectors is substantially perpendicular to the surface of the chest and substantially aligned or parallel with the direction of motion (e.g., substantially straight down toward the spine). The separation distance between the detectors may be small compared to the total distance traveled. In the case of CPR, an average chest compression may be five centimetres and hence, an appropriate separation distance may be, for example, 10% of the total compression or five millimetres. A smaller separation distance may provide an improved position resolution.

At the start of a chest compression, the initial position of the second detector is measured and defined 20. As the first detector moves down toward the second detector during the chest compression, its position is measured 21. Once the position of the first detector approximately matches the initial position of the second detector 22, it may be assumed that the first detector has traveled the five millimetre separation distance. At this point, the system may once again measure and define a new initial position of the second detector and the process may be repeated. Even if a source of distortion is present in the environment, the distortion should affect both detectors equally at the same position in space. Consequently, distortion errors may be mitigated, reduced or eliminated. As the chest compression reaches its deepest point 23 and begins to travel upwards again 24, the position of the first detector may be used to map the coordinate positions.

Once the coordinates along the path of travel have been mapped, position measurements from only one detector may be necessary. However, it may be useful for the process of mapping out the coordinates along the path of travel to be performed regularly or repeatedly (e.g., at fixed time intervals or at trigger events such as start of a compression), so as to account for any new distorters entering the environment that were not accounted for during the first mapping process.

An example method for measuring chest compression depth is now described. In particular, this method may be suitable for use with a system having a compound field detector and field generator as described above.

The positions of at least two coils (e.g., the coils of the compound detector) adapted to move in accordance with the patient's chest (e.g., placed on the chest) are determined. This may be by way of the processor processing received response signals from each coil in response to a detected field from the field generator, as described above. The response signals may represent information (e.g., position information) that may be processed by the processor.

The apparent distance between the coils is estimated. For example, the processor may determine the apparent distance between the centers of the coils, based on the response signals received from each coil.

A correction factor is estimated, based on any differences between the apparent distance and the known and fixed distance between the coils. For example, the processor may have the actual fixed distance between the coils of the compound detector stored in its memory. This actual distance is compared to the apparent distance calculated and a correction factor is calculated accordingly.

The chest compression depth is determined based on the determined positions and the correction factor. For example, the processor may determine the position of the compound detector (e.g., by averaging the position information from the coils of the compound detector) calculate the apparent chest compression depth using known methods and apply the correction factor to get the actual chest compression depth.

The apparent distance between the coils can be determined based on the position information from each coil at a given time (e.g., as described above) or based on the distance as one coil travels from its own initial position to the initial position of the other coil (e.g., as described above).

Figure 13:
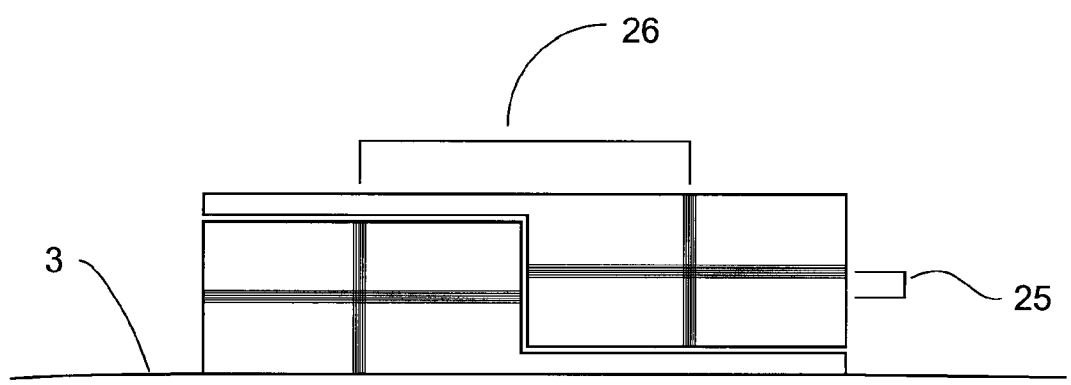
FIG. 13 is an illustration showing two example detectors placed in another example compound detector.

The two field detectors or coil assemblies in the compound detector configuration may be positioned in such a way that their centres are not aligned along the vector path of the chest compression. For example, in addition to being spaced apart in a direction parallel to the expected direction of motion, the detectors may also be laterally spaced apart, for example as shown in FIG. 13. This may allow the detectors in the compound detector to have a lesser spacing in the direction of motion. This may also allow the compound detector to be more compact in size. In this case, the centres of the field detectors retain a fixed and known separation distance 25 along the vector path of the compression but also have a fixed and known lateral separation 26 that must be compensated for as shown in FIG. 13. Although position resolution may be improved by decreasing the separation distance, the lateral separation introduces a vector component in the separation between the detectors that does not lie along the path of motion. This added vector may complicate the mathematical compensation for distortion in the environment.

Figure 14:
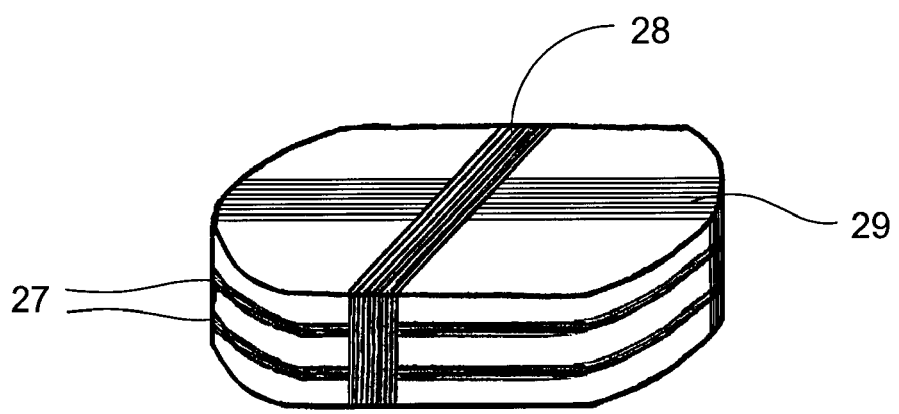
FIG. 14 is an illustration of another example compound detector in which each of the detectors shares one or more common coils.
Figure 15:
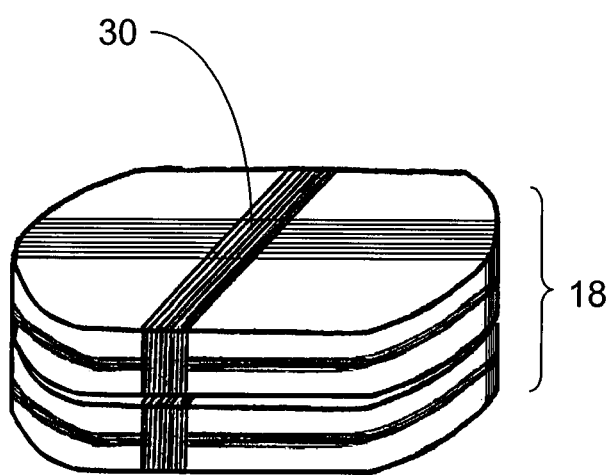
FIG. 15 is an illustration of an example compound detector in which the detectors do not share any common coils.

The compound detector configuration may also include two detectors or coil assemblies in which each of the two detectors may share one or more common perpendicular coils having as shown in FIG. 14. For example, the first detector and second detector may each consist of a Z axis coil 27, but may share the same X axis coil 28 and Y axis coil 29. Computations may account for the centers of the Z axis coils and the X and Y axis coils not coinciding. Despite the increased mathematical complexity, this configuration allows the use of fewer coils, which may decrease costs and/or complexity in manufacturing. For example, in a system that may have required six coils 30 as shown in FIG. 15, four may now suffice.

A compound detector configuration may allow the system to have a lesser sensitivity to the absolute tolerance of the individual detector assemblies. Instead, the relative tolerance of the two detectors may be the more important parameter. For example, if the second detector of the compound detector is mapping the coordinates along the path that will be traveled by the first detector of the compound detector, the more similar the two detectors are, the more similar their position coordinates will be when they are located at the same position in space. Therefore, the two coil assemblies in the compound detector may be wound so that their number of turns, inductance, resistance, area and other parameters are relatively closely matched.

Electromagnetic systems inherently suffer from hemisphere or quadrant ambiguity. Depending on the number of coils in each detector and generator configuration, the received signals may be identical in opposite quadrants or opposite hemispheres. Certain quadrant ambiguities may be resolved by determining the phase of the detected signals. However, when only two detector or generator coils are used instead of three, it may be impossible to determine the quadrant of operation. When three detector and three generator coils are used, it may be possible to determine the quadrant of operation, but not the hemisphere. Using a compound detector configuration may enable certain hemisphere ambiguities to be resolved.

Figure 16:
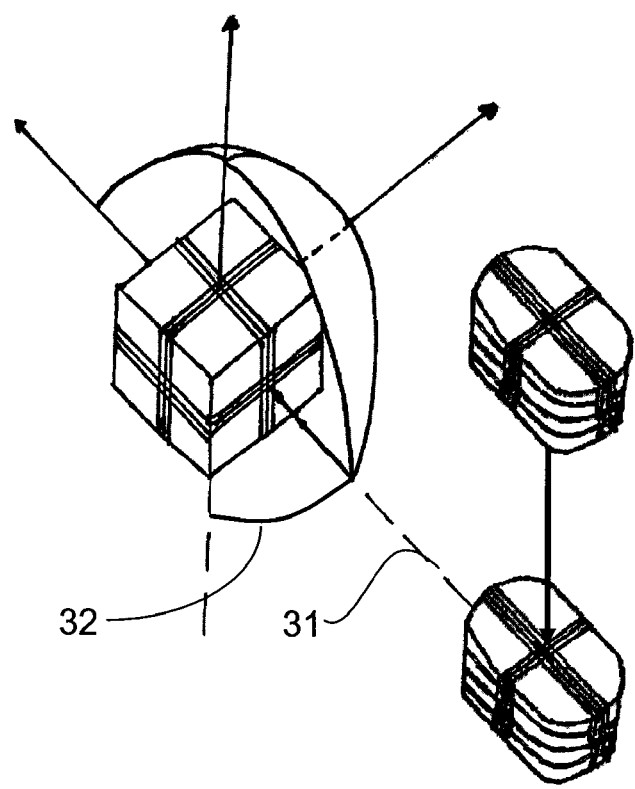
FIG. 16 is an illustration showing a compound detector moving from between two quadrants in space.

For example, in the case of CPR, a change in quadrant as the detector is moved through the chest compression may cause an unexpected change in position. If the compression occurs along the Z axis of the detector coil, and the generator is positioned such that the detector may move from above the generator to down below the generator, an axis 31 may be crossed and a new quadrant 32 may be entered as shown in FIG. 16. In such a case, the first detector of the compound detector will cross the axis before the second detector of the compound detector. Once the first detector crosses the axis, its Z coordinate value may begin to increase while the Z coordinate value of the second detector continues to decrease. This difference in the direction of travel of each of the detectors may indicate that the compound detector is crossing an axis and the appropriate signs may be attributed to the measured coordinates.

Providing a compound detector having two detectors with their centres aligned along the path of the chest compression in a known distance apart may result in a further advantage. The two detectors may facilitate the relatively accurate calculation of a plane perpendicular to the movement of the chest compression. Calculating the normal vector for the plane may be relatively simple as there are two points along the vector available: the centres of each of the two field detectors in the compound detector. The normal vector formed by each of the field detector centers may be used to relatively efficiently and accurately calculate a plane representing the start of the compression. This plane may be used to calculate compression depth as previously described.

In general, although the compound detector is described above as including two spaced apart detectors or coil assemblies, it should be understood that the compound detector may include more than two spaced apart detectors or coil assemblies. Further, although the detectors or coil assemblies within the compound detector are shown to be relatively similar, they may also be dissimilar in dimension, number of turns, inductance, resistance, etc.

Figure 17:
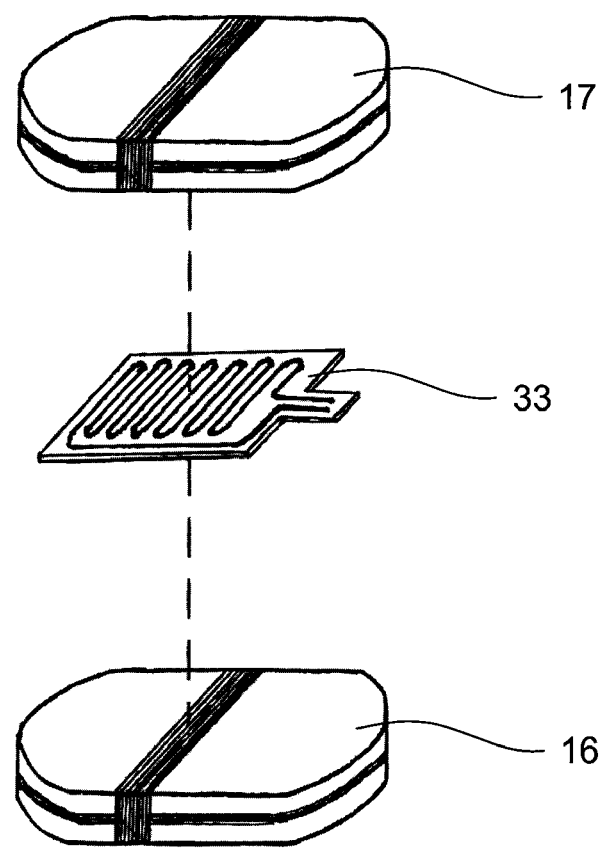
FIG. 17 is an exploded view of an example compound detector having an example force sensor.

In another embodiment, a sensor 33 or material capable of measuring force, pressure or contact is provided with the field sensor, for example between each of the field generator detectors in a two-detector compound detector system as shown in FIG. 17. The two field detectors may be used to compensate for distortion and improve accuracy of the system as described above. The force, pressure or contact sensor is used to measure the force or contact exerted by the user on the patient's chest during the compression. In the case of a force and/or pressure sensor, the force signal may be used to further improve the measured position data. For example, a force or pressure signal may be correlated with the position signal to filter out noisy data and signal distortion.

The force, pressure and/or contact sensor may also be used to achieve a more accurate measure of chest recoil. The sensor may be used to detect when complete release of the chest following a compression has been achieved. The field data alone may be used to measure adequate chest recoil by measuring the extent to which a chest compression returns to its home or starting position. However, the chest may lose compliance over time and the starting position may change over time. In this instance, a pressure sensor may help enable more accurate chest recoil determination.

The position data from the field detectors may also be used to measure the compliance of the patient's chest. By measuring the total force applied by the user to compress the patient's chest a certain distance (as measured by the field detector/generator), a compliance constant may be determined that correlates the force signal to the chest compression depth for that specific patient. This compliance constant may have a number of uses. For example, if the system determines that its power level is below a given threshold (e.g., where the system is powered by a battery), the system may enter a mode in which position and/or depth information is based solely on the force data. For example, the first compression of each cycle of thirty may be used to calculate a compliance constant that is used to convert all of the following force measurements into position data.

Beyond power conservation benefits, this design strategy may also allow the system to operate in a very noisy or highly distorted environment with relatively little or no ill-effects. Furthermore, the force sensor may allow the system to continue operation even if the reference sensor is moved during the administration of the chest compressions. For example, if the reference sensor is kicked accidentally while CPR is being performed, the detected sudden movement may trigger the system to automatically switch to determining position information using data from the force sensor until the reference sensor is determined to be relatively stationary again. This may prevent an interruption in the determination of compression depth and/or delivery of depth feedback to the user. Such sudden movements of the base may be determined by comparing the force data from the force sensor and position data from the position sensors. Any severe incongruities in the two sets of data may denote a sudden shift in position of the reference sensor. Incongruities between the force sensor and position sensor may also indicate that other sources of noise or distortion have entered the operating environment.

Another example benefit to the incorporation of a force sensor within or on the position sensor is hemisphere ambiguity resolution. Typically, using dot products calculated from the position vectors in the 3×3 signal matrix, the quadrant and hemisphere of operation may be resolved. However, the ambiguity resolution using dot products does not eliminate ambiguity across hemisphere. Nevertheless, a force or pressure sensor may be used to detect the crossing of a hemisphere boundary of the system. When crossing a hemisphere boundary, the position coordinates may have the incorrect sign. This may result in an erroneous compression depth. It may appear as though the compression is traveling upward rather than downward. By monitoring the direction of travel with the force sensor, the signs of the coordinates in each hemisphere may be corrected and the direction of travel may be determined.

Although the previous description incorporating a force, pressure or contact sensor into the field detector assembly refers to an example embodiment in which the two field detectors of a compound detector are sandwiching the force sensor, other embodiments are possible. For example, there may only be one field detector rather than a compound detector, with the force, pressure or contact sensor placed on either the front surface of the field detector (e.g., against the palm of the user) or the back surface of the field detector (e.g., against the patient's chest).

A major source of position error in an electromagnetic tracking system is distortion resulting from the presence of metallic objects in the tracking environment. Specifically, highly conductive metals are particularly problematic due to the generation of eddy currents within them. These eddy currents produce an electromagnetic field that bucks the magnetic field radiating from the field generator. The use of two field detectors in a fixed location relative to each other, in a compound detector, may reduce the effect of the distortion as described above. However, other methods of distortion compensation may be used in environments known to be filled with or encapsulated by large quantities of metal. For example, CPR is often performed inside an ambulance. The frame of the ambulance may consist of aluminum sheets capable of producing large eddy currents that may be detected by the field detector resulting in distorted data. In a known and fixed environment, such as inside an ambulance, the field distortions may be mapped for future reference by the system.

For example, at each point in the operating environment, the field distortion may be measured empirically and a lookup table or compensation equation (e.g., a polynomial fit) that represents the measured distortion may be stored within the system's processor memory as a distortion map. When a certain distortion is measured and matches a known distortion stored in memory, the processor use the corresponding distortion map to correct for that known distortion. For example, the correct position for that data may be found within the look-up table or by using the distortion compensating equation. The use of the distortion map may be initiated automatically by the processor (e.g., in response to the detection of the known distortion) or may be in response to selection by the user. Where a known distortion is detected by the processor, the processor may ask the user to confirm whether or not to correct for the known distortion (e.g., through a dialog box provided via the feedback component) before using the distortion map.

For example, since most ambulances have a similar structure and metallic composition, it may be possible to incorporate a generic "ambulance mode" into the system that may be activated when performing CPR inside an ambulance, in which the system consults the stored distortion map to correct for any distortion arising from the known environment. It may also be possible to automatically detect the presence of distortion caused by the frame of an ambulance. The system may recognize the distortion signature caused by the typical structure and properties of an ambulance's shell. Upon detection of the distortion signature, the system may automatically begin operation in a distortion-compensation mode by using the pre-determined distortion map corresponding to the detected distortion signature.

Figure 18:
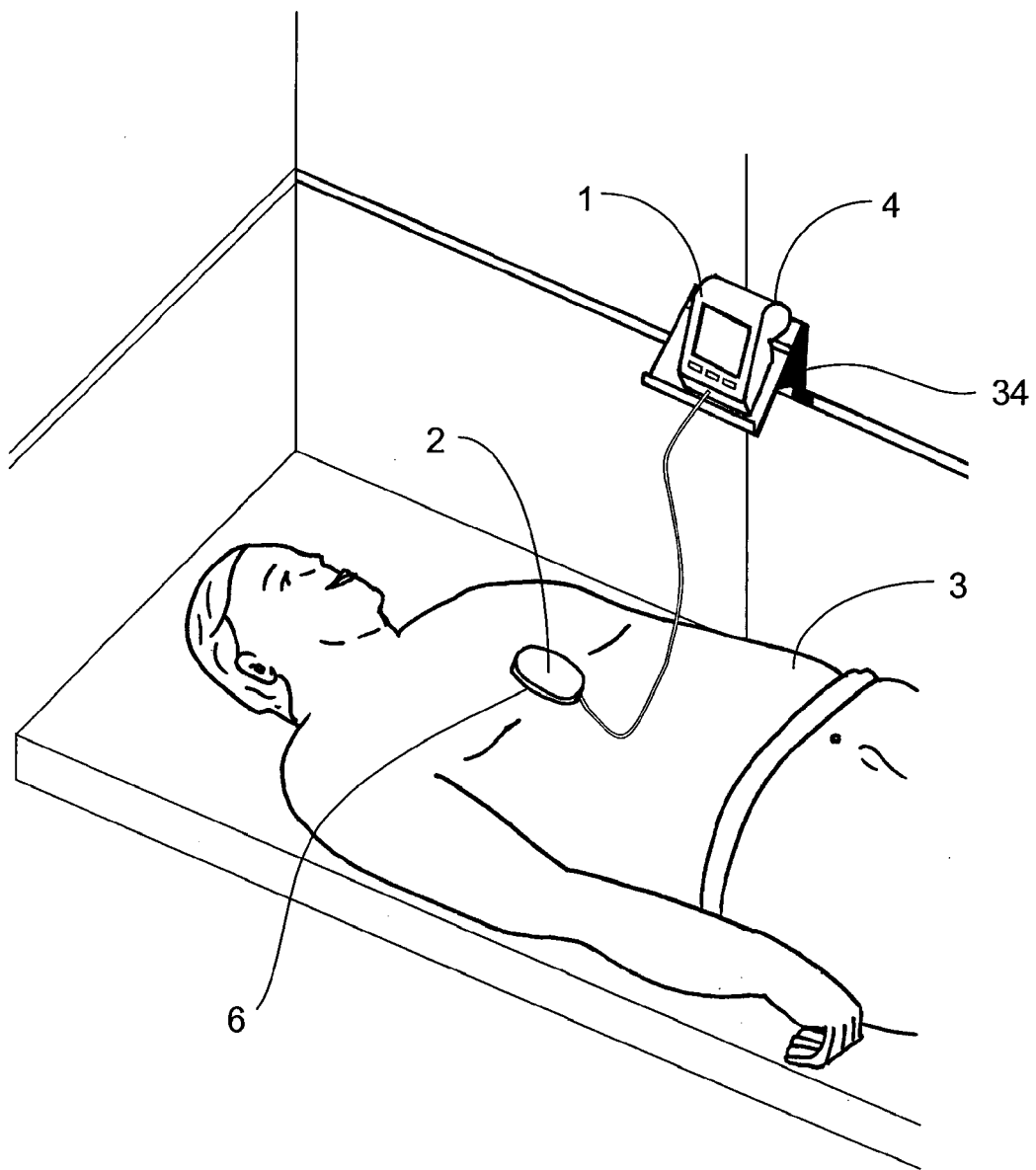
FIG. 18 is an illustration showing an example base unit containing an example reference sensor placed in a holder on the wall of an ambulance and an example position sensor on the chest of a patient.

The system may also have an automatic calibration mode where the system is placed in a specified location (e.g., defibrillator brackets 34 in an ambulance) and the environment is surveyed for distortion, for example as shown in FIG. 18. This type of distortion compensation may not be as effective as mapping out the environment in advance, but it does not require previously stored information.

A designated distortion mode may also take advantage of a force or pressure sensor embedded within the field detector. For example, in such a mode, the system may rely more heavily on the force sensor to assist in removing the distortion from the signal. If the patient is moved from a non-distorted location (e.g., pavement) to a distorted environment (e.g., ambulance), the system may use force sensor calibration constants calculated in the non-distorted environment for proper operation in the distorted environment.

Metallic objects are one source of potential error and distortion for the system. Another source of error involves out-of-phase movement between the field detector and field generator. Any movement of the reference sensor during the administration of CPR is a potential source of error as all measurements are relative to the reference sensor. The system may be configured to recognize any movements of the reference sensor. These movements are typically large and sudden and may be easily filtered using various signal processing techniques. Movements of the reference sensor may also be determined by placing a motion detecting sensor, such as an accelerometer, next to or within the reference sensor. The accelerometer may be used to alert the processor that the reference sensor (e.g., field generator) is not stationary. When the reference sensor is moved, the system may temporarily stop sending position and/or depth feedback to the user. Once the movement of the reference sensor has ceased, the system may recalibrate a starting position for calculating compression depth and resume determination of position information and resume providing feedback. If a force or pressure sensor is embedded within the position sensor, calibration may be performed by determining when the chest has been fully released (i.e. when the force exerted on the chest is at a minimum). At this point, the system may determine that the compression is at its starting point. Furthermore, a force or pressure sensor may allow the system to continue operating during a movement of the reference sensor. For example, if the system detects that the reference sensor is moved, the position data may be temporarily based on the force data rather than the data from the field detector/generator. As previously described, the force sensor may be first calibrated by using the position data collected from the field detector/generator.

When an accelerometer is placed in proximity to the reference sensor, the movement of the reference sensor may be determined and may be filtered out of the position data. For example, a tri-axial accelerometer may determine motion of the reference sensor in the x, y and z axes and this motion may be subtracted from the motion sensed in the three axes by the position sensor.

Oftentimes, CPR is performed on a patient supported by a non-rigid surface such as a mattress. When a chest compression is delivered to a patient on a mattress or other flexible material, the chest undergoes two distinct movements. The first movement is that of the chest being compressed inward by the hands of the user. The second movement is that of the torso moving into the soft surface of the non-rigid surface. Only the movement of the compression itself is useful in forcing blood through the circulatory system of the patient. However, a typical CPR assist system may not be able to distinguish between the two distinct movements and may measure a larger compression depth than what may have actually been delivered. Therefore, the system may indicate to the user that each chest compression is deeper than it is resulting in shallower compressions.

A number of potential methods may be used for dealing with this situation. For example, given the three components of a first detector, a second detector and a generator, one component may be adapted to move in accordance with the non-rigid surface (e.g., placed on the mattress below the patient), a second component may be adapted to move in accordance with the patient's chest (e.g., placed on the patient's chest), and the third component may be adapted to be stationary relative to the patient. The actual depth of compressions may then be determined by determining the relative motion between the component (e.g., the first detector) moving with the non-rigid surface and the component (e.g., the second detector) moving with the patient's chest, for example by subtracting the position of one from the position of the other.

Figure 19:
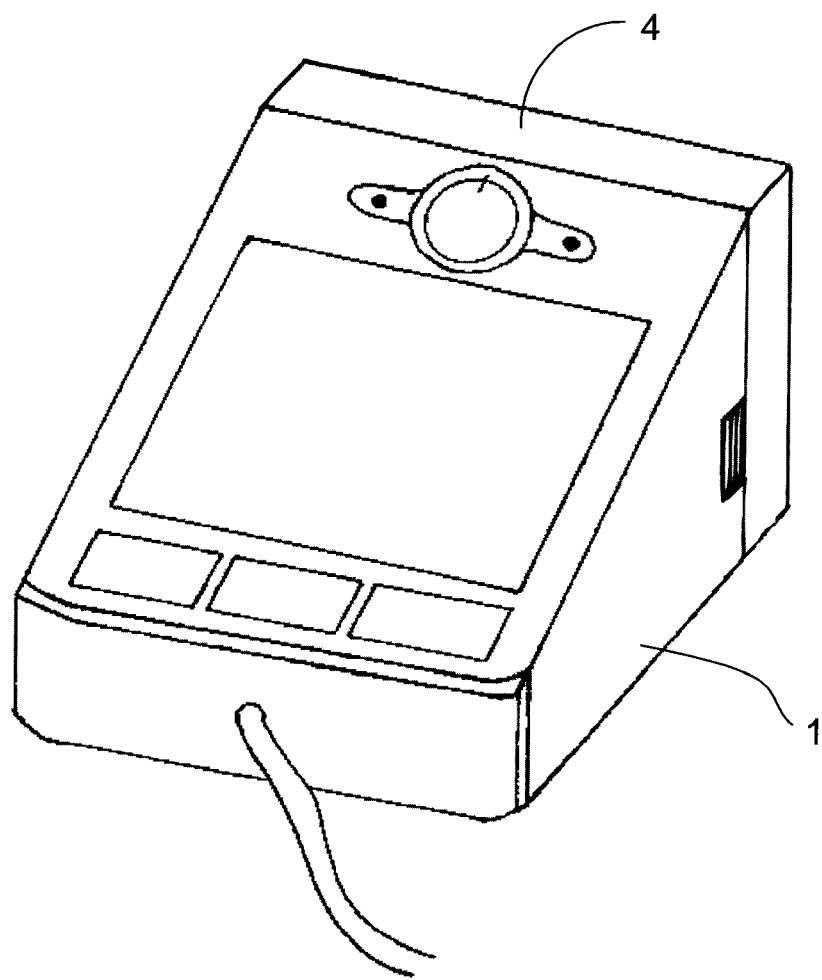
FIG. 19 is an illustration of an example base unit with an example detachable position sensor in its off configuration.
Figure 20:
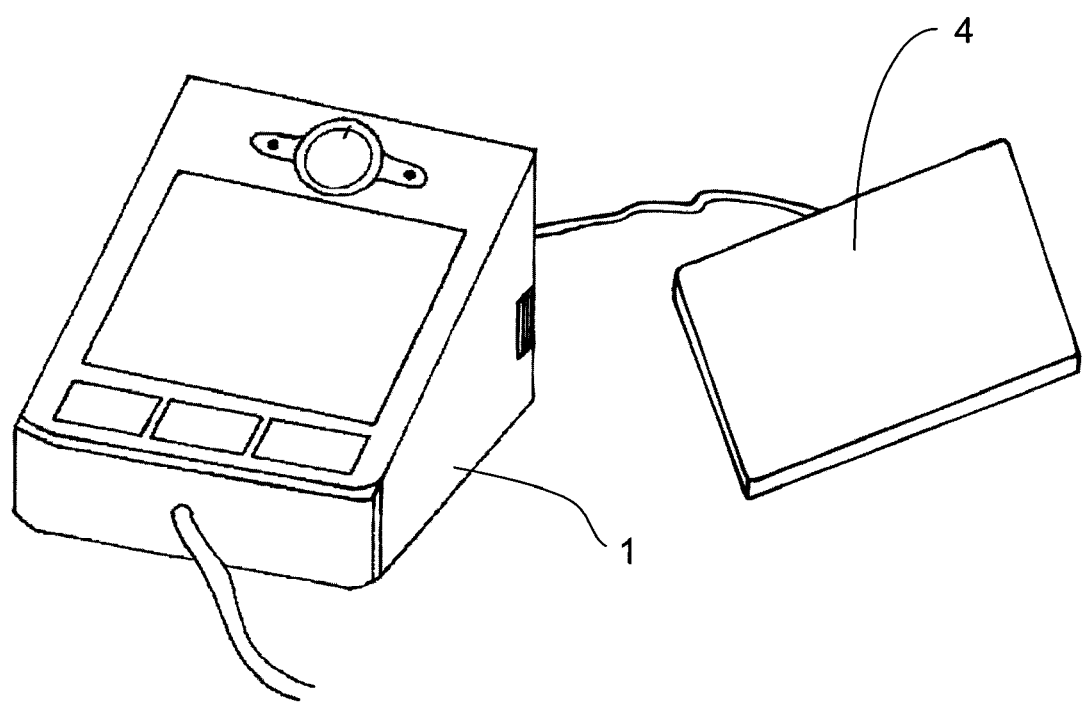
FIG. 20 is an illustration of an example base unit with an example detachable position sensor detached from the unit and ready for use.
Figure 21:
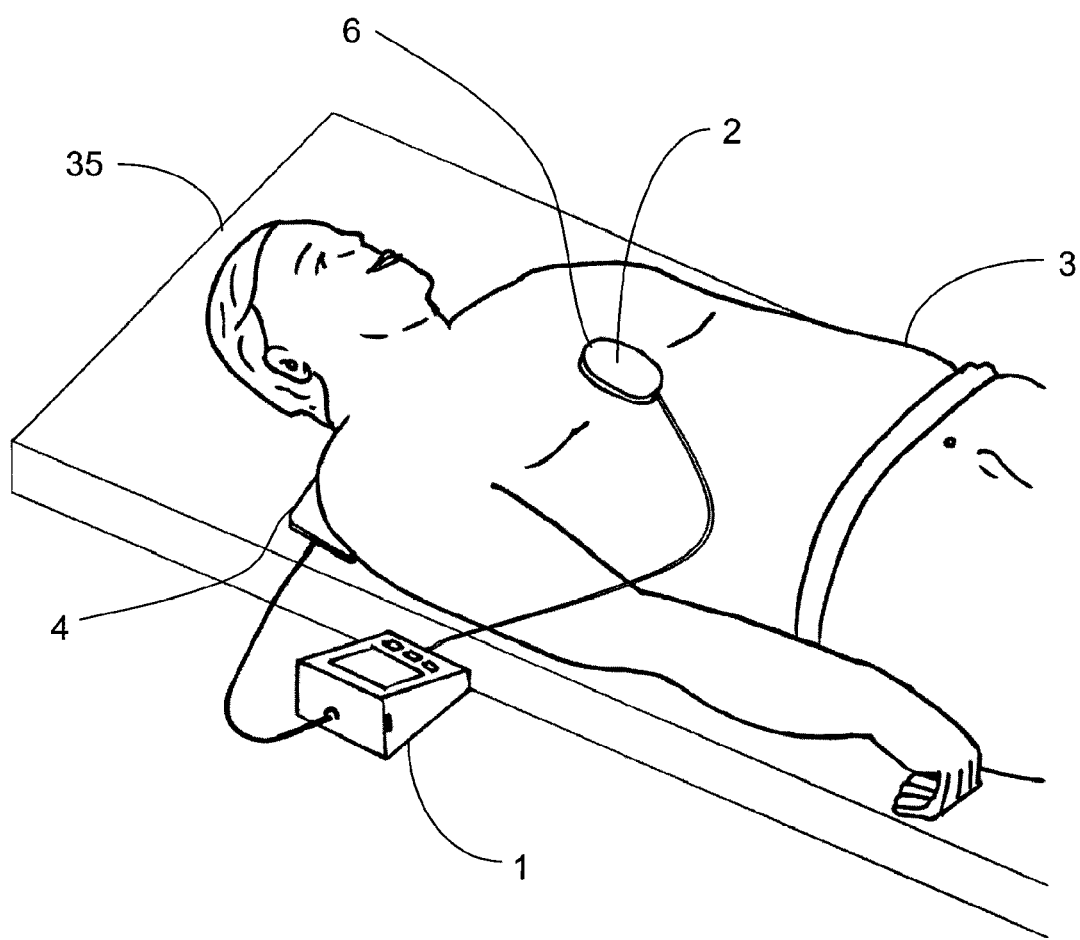
FIG. 21 is an illustration showing an example field generator detached from its base unit and placed under the patient and an example field detector placed on the patient's chest.

In an example embodiment, the field generator may be detachable from the base unit of the system as shown in FIG. 19 and FIG. 20. For example, if the base unit is a defibrillator, the field generator may be removable from the defibrillator. The field generator may be positioned on the mattress 35 underneath the patient as shown in FIG. 21, adhered to the back of the patient or sandwiched between the mattress and the patient's back. The field detector 2 may be positioned on the sternum of the patient. As a chest compression is administered, the field generator may move with the mattress, while the field detector may move with the combined motion of the mattress and the chest of the patient. The position of the field detector is measured with respect to the field generator and thus, the movement of the mattress is effectively eliminated since the field generator and field detector are both subjected to that same movement.

Figure 22:
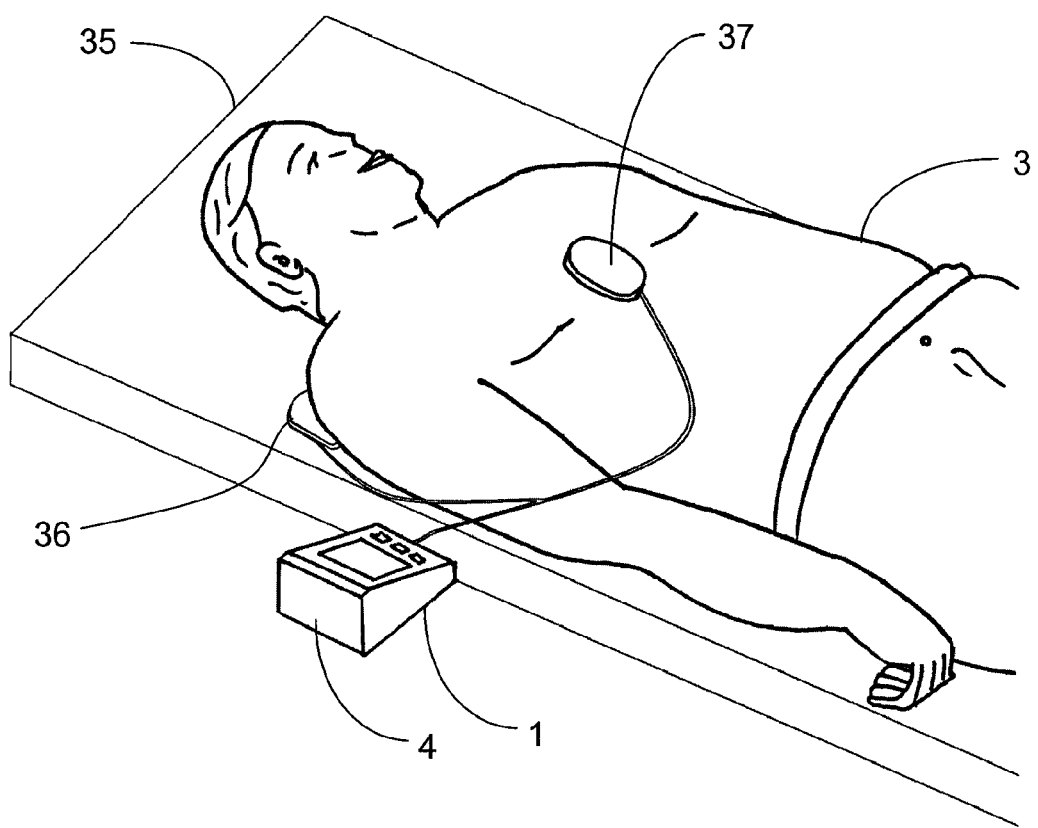
FIG. 22 is an illustration showing an example field generator in a base unit and two example field detectors, one placed under the patient and one on the patient's chest.

In another example embodiment, there may be two field detectors and one field generator as shown in FIG. 22. The field generator may be in the base and one of the field detectors may be placed on the chest of the patient. The second field detector 36 may be placed on the mattress underneath the patient, adhered to the back of the patient or sandwiched between the mattress and the patient's back. Therefore, the second field detector may move with the mattress and may determine the amount of motion experienced by the mattress during a chest compression. The first field detector 37 may experience the combined motion of the chest compression and the mattress. Therefore, the processor may subtract the movement of the second field detector from the movement of the first field detector thereby eliminating the movement of the mattress from the chest compression depth measurement.

Figure 23:
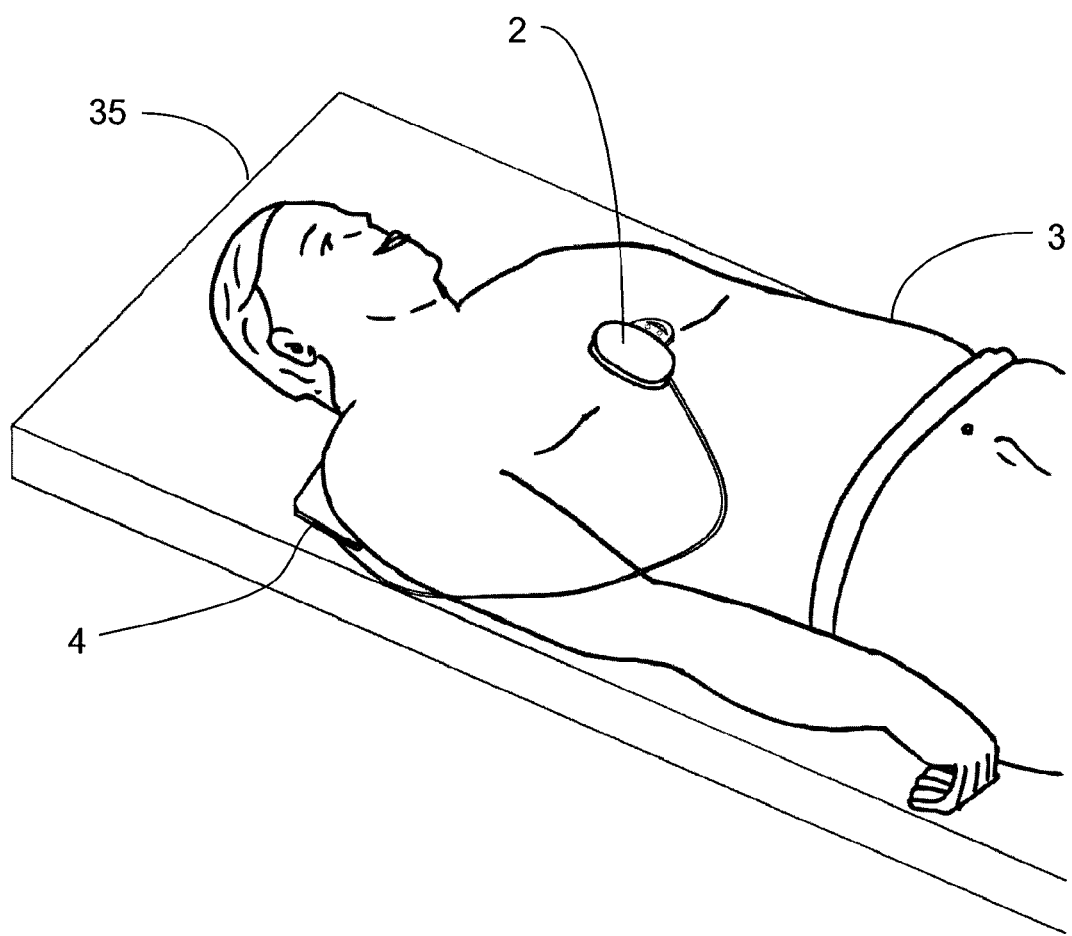
FIG. 23 is an illustration showing an example reference sensor placed under the patient and an example position sensor placed on the patient's chest with feedback provided on an example position sensor.

In another example embodiment, there may not be a base unit. The system may comprise a field generator and a field detector in which the field generator is placed underneath the patient and the field detector is placed on the chest of the patient as shown in FIG. 23. As described in the previous embodiments, the movement of the mattress may be easily subtracted from the compression depth calculation. Other embodiments in which the placement of the field generator and field detector are interchanged are also possible.

Methods of compensation may be required for other possible situations. For example, the chest of the patient may lose compliance over time. As CPR is performed, the chest may sink and there may be less elasticity in the internal structures. This may result in a drift of the actual starting position of the chest compressions over time. The system may compensate for a loss of chest compliance and a change in starting position of the compressions by recalibrating the start position (e.g., top of the chest compression) before each cycle of chest compressions. For example, if each CPR cycle consists of thirty compressions and two rescue breaths, the system may recalibrate the compression start position during the administration of the two breaths. If continuous compressions are being delivered, absent of any interruptions, the system may calibrate using a force or pressure sensor. The system may determine the starting position of a compression by detecting the point where the minimum amount of force is exerted by the user on the chest.

Oftentimes CPR must be performed in a moving environment. For example, CPR is regularly administered inside a moving ambulance or medical helicopter. Furthermore, CPR may be performed inside larger vehicles such as trains, planes or large ships. Current compression depth methods employing accelerometers may register the external movements of these vehicles as a part of the chest compressions. The accelerometer measures acceleration relative to the Earth and it may be relatively difficult for the accelerometer to isolate the compression movement from that of the vehicle. By using an external reference sensor, the movement due to a vehicle may be easily eliminated. For example, the reference sensor may be placed within the vehicle or moving environment and all measurements by the position sensors are made relative to the reference sensor. Therefore, any movement experienced by both the reference sensor and the position sensors may be effectively ignored or taken into account by the system.

Figure 24:
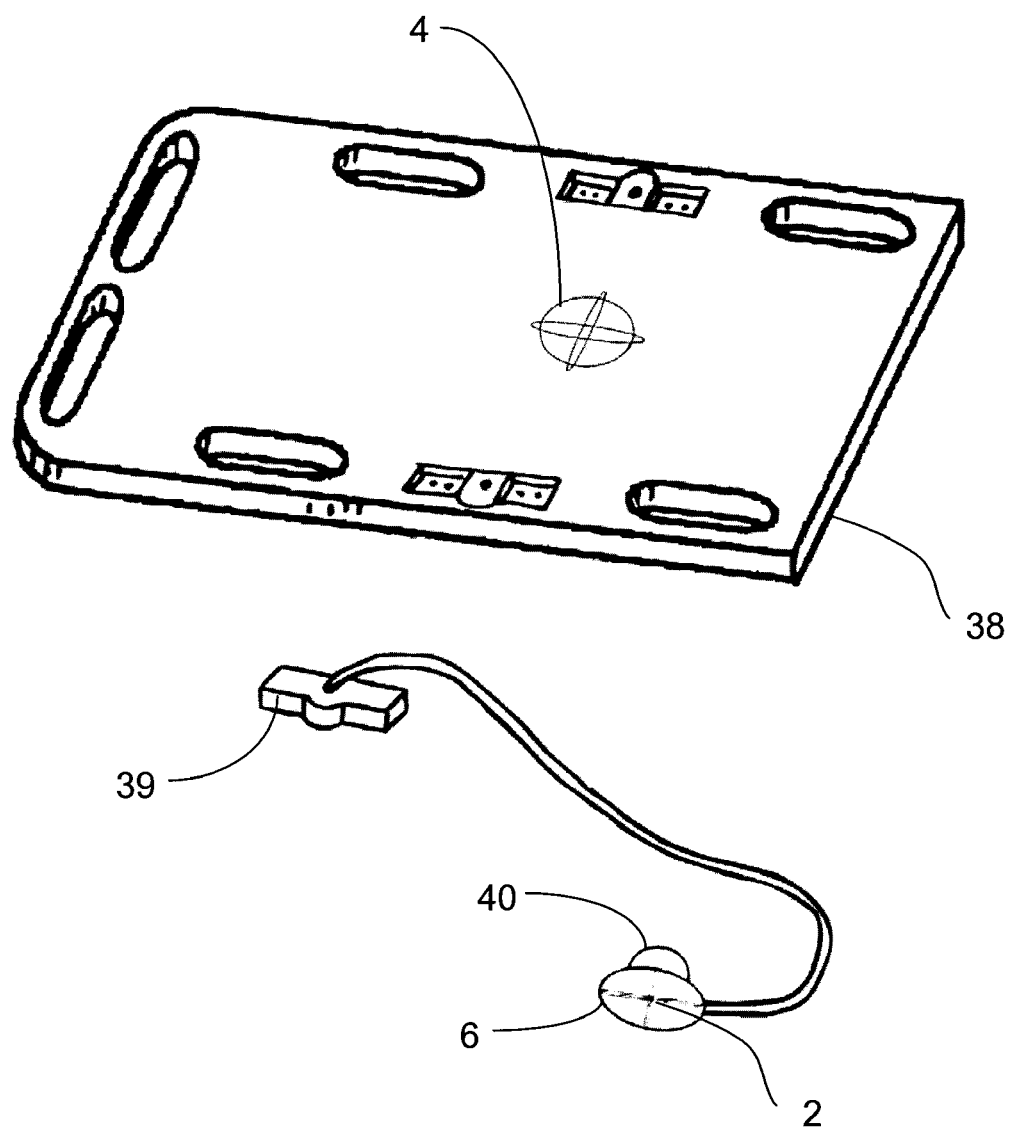
FIG. 24 is an illustration showing an example patient backboard with an example reference sensor embedded in the backboard.

Other moving environments beyond vehicular transport of a patient are possible. For example, a patient may be transported on a gurney, stretcher or backboard 38. As shown in FIG. 24, the reference sensor may be placed on or within the backboard 38. The position sensor may be connected with a connector 39 into the backboard and the feedback 40 may be provided on the pad housing the position sensor.

Figure 25:
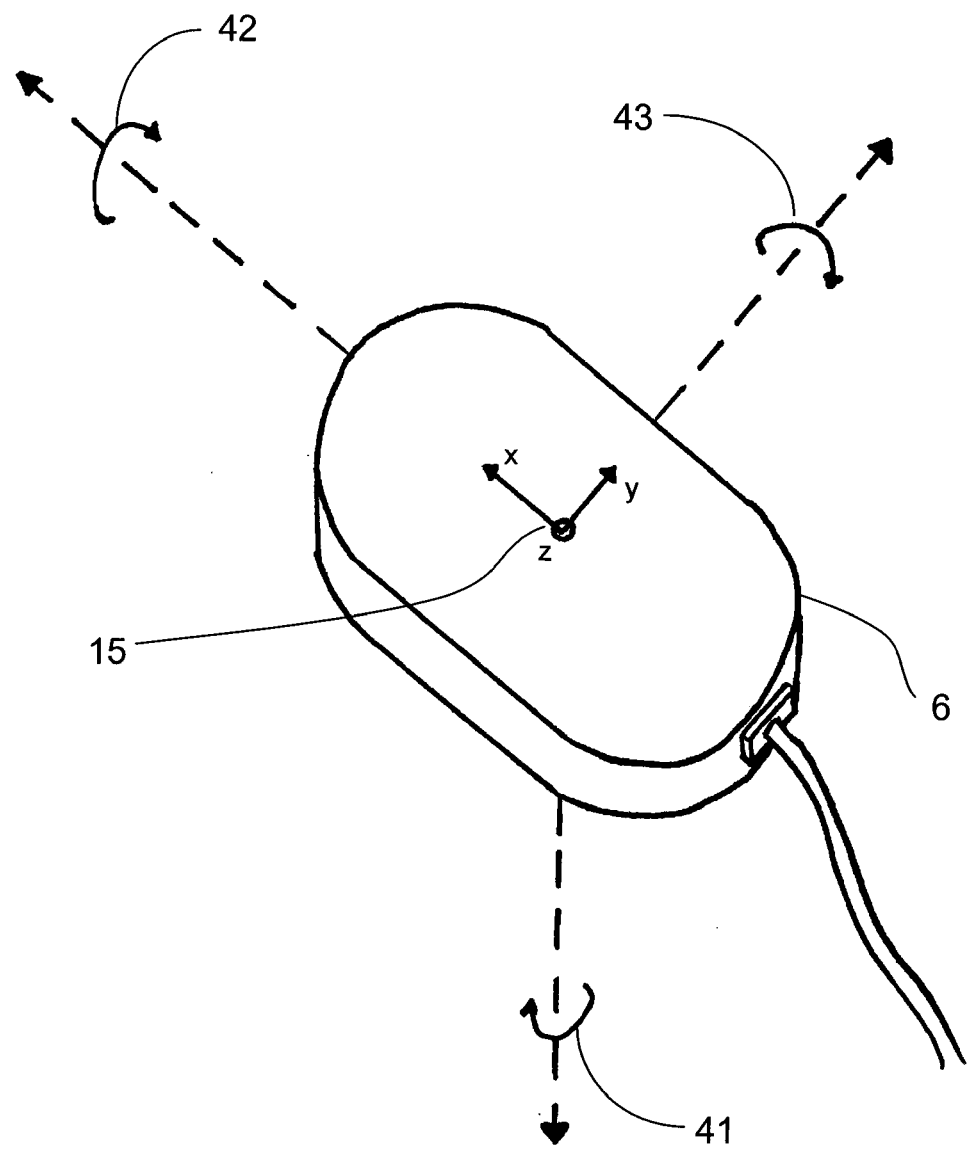
FIG. 25 is a diagram showing the angles of rotation of an example pad housing an example position sensor.

The orientation of the position sensor may be determined using calculations disclosed in U.S. Pat. No. 4,314,251, the disclosure of which is hereby incorporated in its entirety by reference. The roll 41, pitch 42 and yaw 43 may be used to determine the three dimensional configuration of the position sensor as shown in FIG. 25. During CPR, the starting configuration and orientation of the position sensor relative to the chest of the patient may be known. When placed inside a puck or pad 6 positioned on the patient's chest, axes 15 or other markings may be labeled on the position sensor housing indicating proper orientation of the system. The tilt of the position sensor may then be calculated and factored into the depth calculation. If the position sensor is placed unevenly on the chest, the orientation angles may be used to correct the depth calculation. Furthermore, the calculated angles may be used to rotate the frame of reference for the position sensor. For example, the position information may be rotated into the position sensor's reference frame to simplify calculations and improve accuracy.

Figure 26:
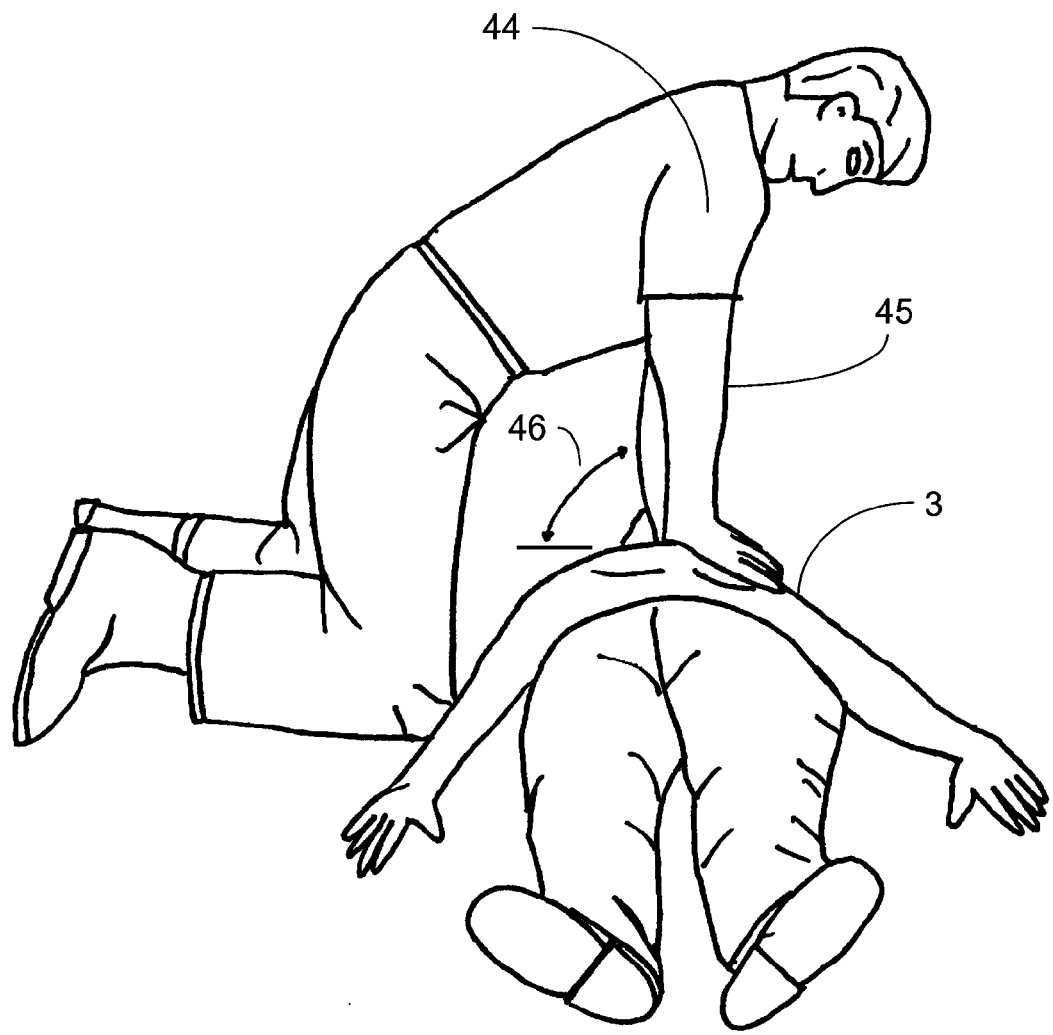
FIG. 26 is an illustration of a user performing CPR in an example of proper form.
Figure 27:
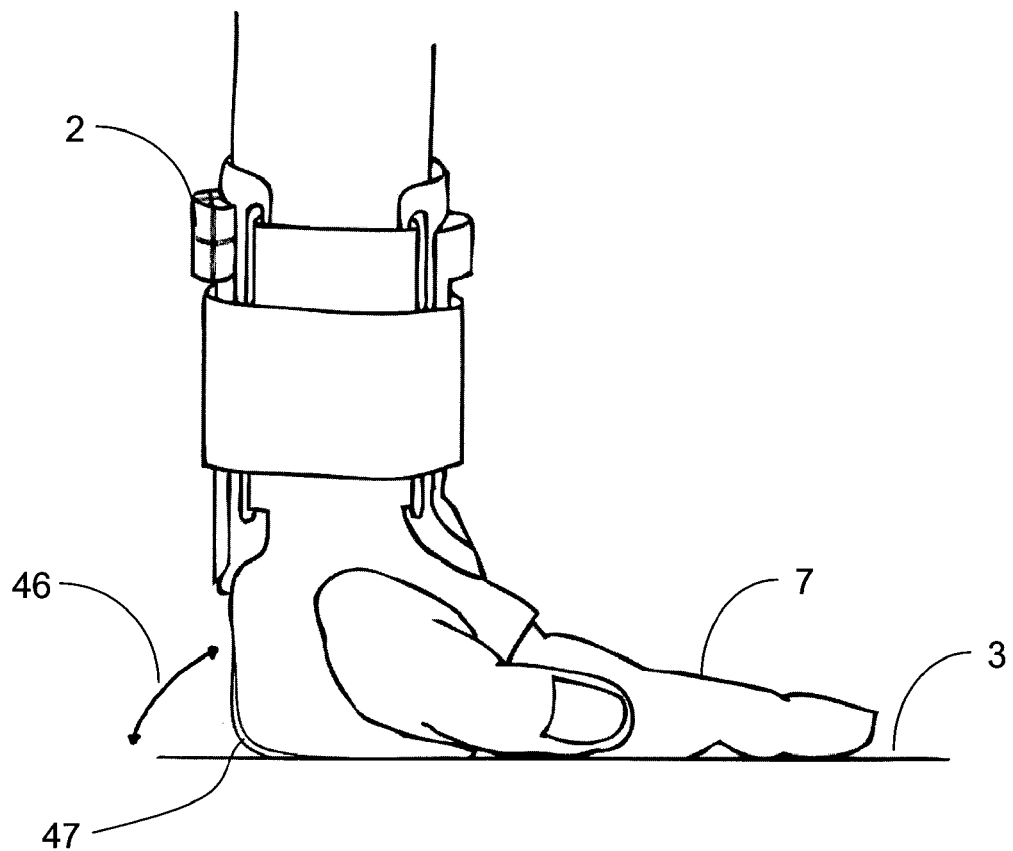
FIG. 27 is an illustration showing an example wearable embodiment of the CPR assist system.

CPR is physically demanding and user fatigue often results shortly after commencing chest compressions. Ineffective technique and improper physical form may lead to a faster onset of fatigue and pain associated with prolonged administration of CPR. When delivering compressions, the user should have his or her shoulders 44 positioned directly over the body of the patient with his or her arms 45 locked, straight and perpendicular to the patient's chest as shown in FIG. 26. The system may be used to monitor the angle 46 of chest compressions by housing the position sensor within a wearable embodiment of the system as shown in FIG. 27. For example, the position sensor may be housed in a wrist band or glove that positions the sensor on the wrist of the user. The roll, pitch and yaw angles may be used to determine the relative orientation of the user's arm. The user may then be prompted to adjust his or her arm angle 46 to maximize the transfer of force during CPR and reduce user fatigue. To reduce distortion and error in the angle measurement, the wearable system may incorporate a bend sensor 47 that varies its resistance with the degree of bend. The sensor may be used to measure the bend of the wrist of the user. This data may be correlated with the field data to improve accuracy. The bend sensor serves a similar function for angle as the force or pressure sensor does for depth.

Figure 28:
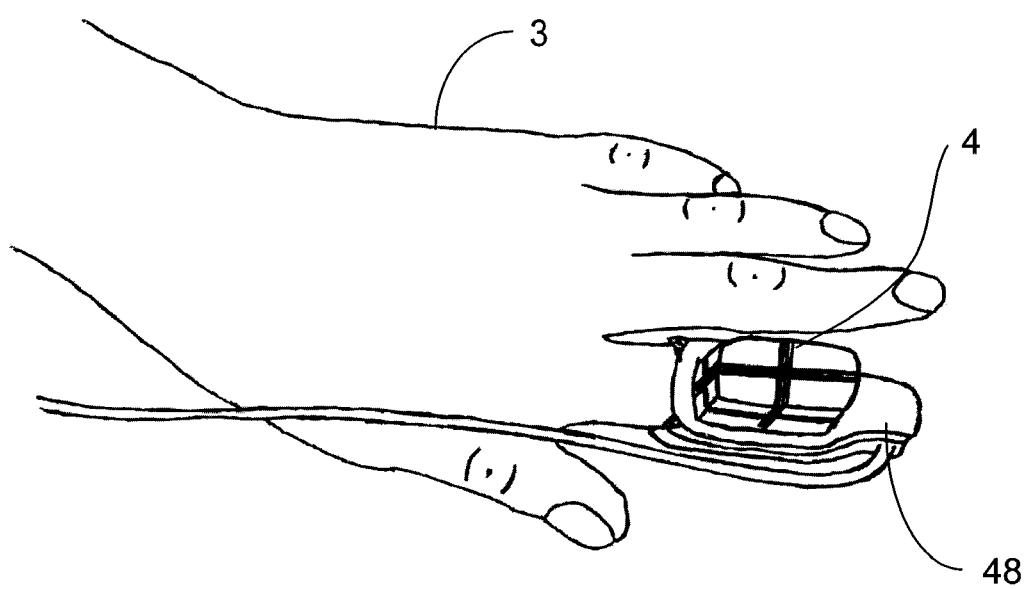
FIG. 28 is an illustration showing an example reference sensor position on or adjacent to a pulse oximetry device.

Different methods of combining various sensors with the field detector and field generator may be used to improve positional accuracy and correct for distortion and/or noise. The system may also be combined with other sensors. As previously described, accelerometers may be used to detect external motion such as movement of the base unit or reference sensor when it is moved during CPR. An accelerometer may also be used to verify the data collected from the field detectors and eliminate metallic sources of distortion. The system may also be combined with pulse oximetry to monitor blood flow through the patient and correlate the blood flow to the field data for increased accuracy. For example, the reference sensor may be incorporated into a pulse oximetry unit 48 on the patient's finger or forehead as shown in FIG. 28.

Figure 29:
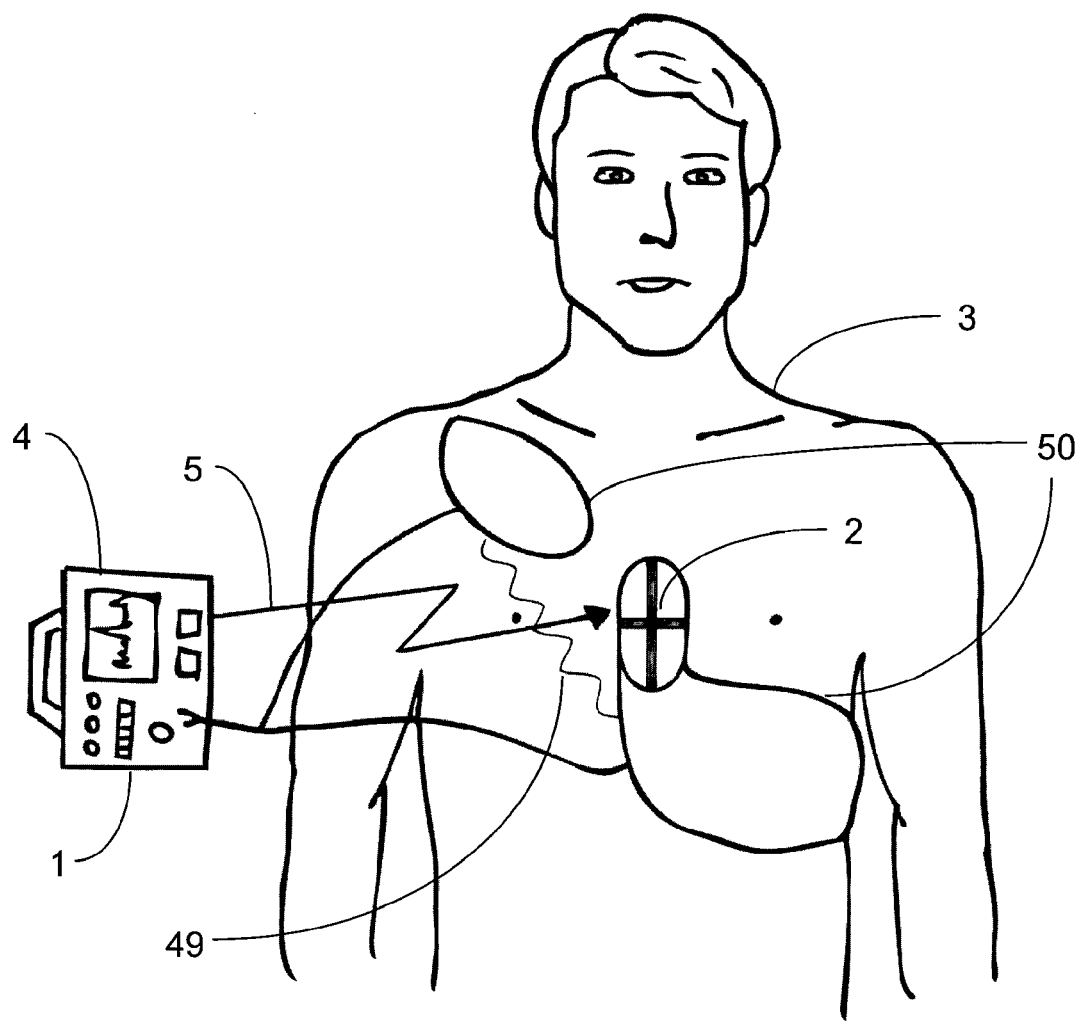
FIG. 29 is an illustration showing a chest impedance measurement between the pads of a defibrillator with an example position sensor embedded in one of the pads.

The system may also incorporate chest impedance measurements. Chest impedance 49 may be used to detect motion of the patient's chest by measuring impedance between two electrodes, such as defibrillator pads 50 as shown in FIG. 29. Chest impedance measurements may serve a similar function as the force sensor measurements in the present system. The chest impedance measurements may be correlated to the field data to improve accuracy and remove sources of distortion from the measurements. Furthermore, the field data may be used to calculate calibration constants for the chest impedance measurements that correlate the chest impedance to compression depth. In this way, the chest impedance may be used for depth data when the reference sensor is moved during the administration of chest compressions or if the system is used in a highly distorted environment. As many defibrillators already have chest impedance measurements incorporated within them, the field data may be easily adapted to transform the impedance data into a more useful and more accurate parameter.

Figure 30:
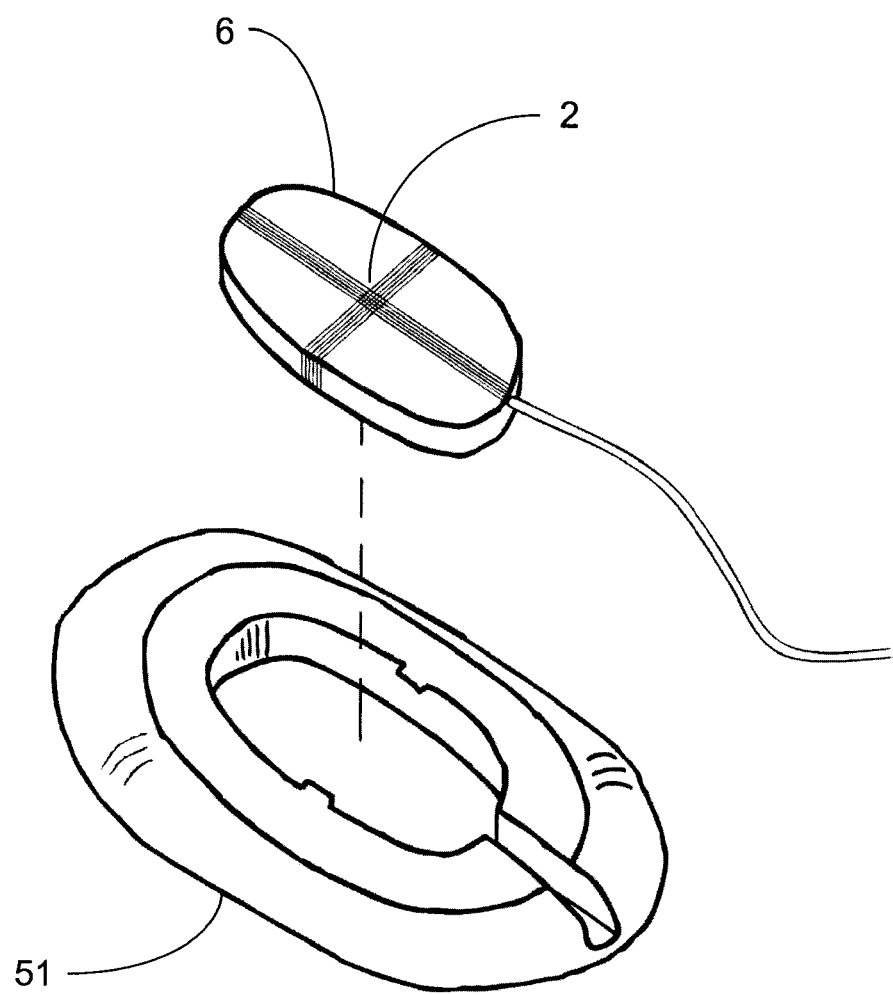
FIG. 30 is an illustration showing an example removable housing for an example position sensor.

The presently disclosed system may be adaptable for different patients. As the position sensor placed on the patient's chest may be made very small and lightweight, it may be adapted for used on an infant or adult. For example, the position sensor may be placed in a removable housing 51 for adult CPR as shown in FIG. 30. The housing may provide a larger surface area and be configured for two handed CPR. When removed, the position sensor may be smaller and more suitable for two-finger CPR on an infant.

Figure 31:
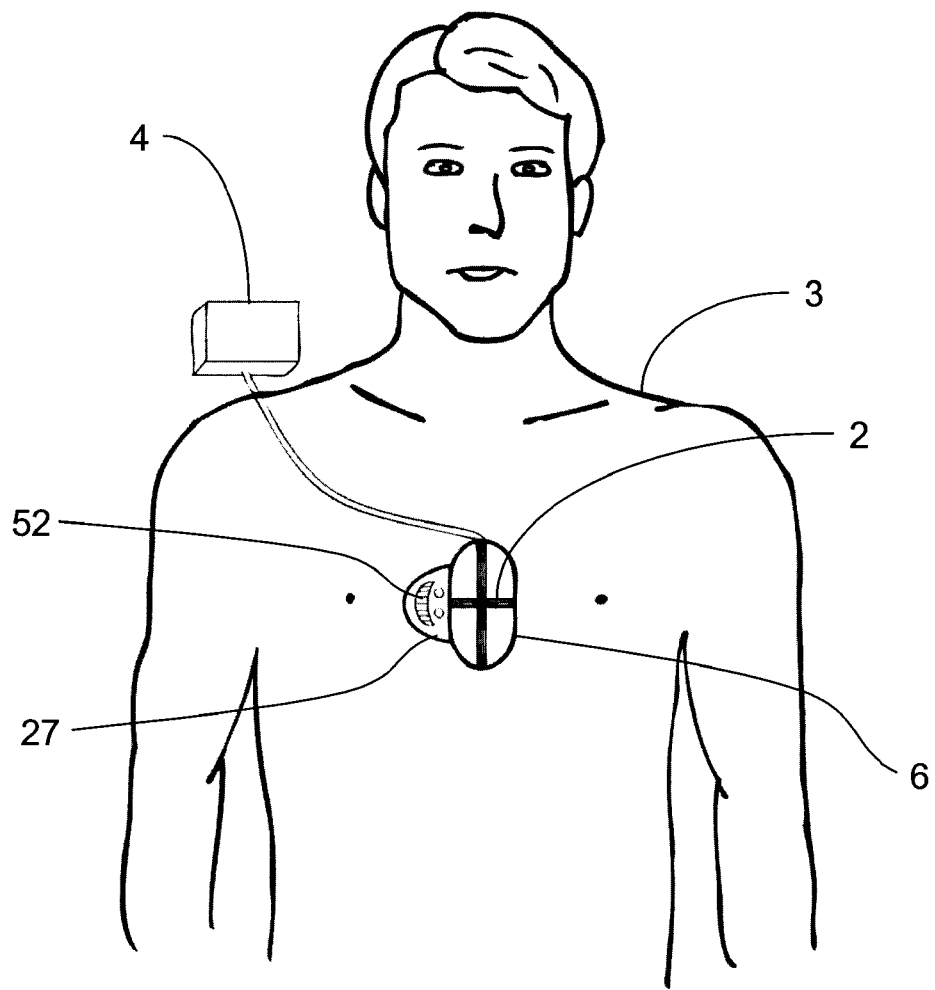
FIG. 31 is an illustration showing an example position sensor with feedback provided on the position sensor.

The presently disclosed system may be implemented in a number of embodiments and feedback may be transmitted to the user in various forms, via a feedback component (e.g., screen, speaker, lights, buzzer, etc.). For example, the feedback may be audible, visual or both. The feedback may be displayed on an LCD display within the base unit. It is also possible that the feedback be incorporated into the position sensor pad 6 itself as shown in FIG. 31. The feedback on the pad may be a display or may be in the form of LED graphics 52. The audio feedback may be delivered through a speaker within the base or within the position sensor pad. The audio feedback may be in the form of voice prompts and/or a pacing metronome.

Figure 32:
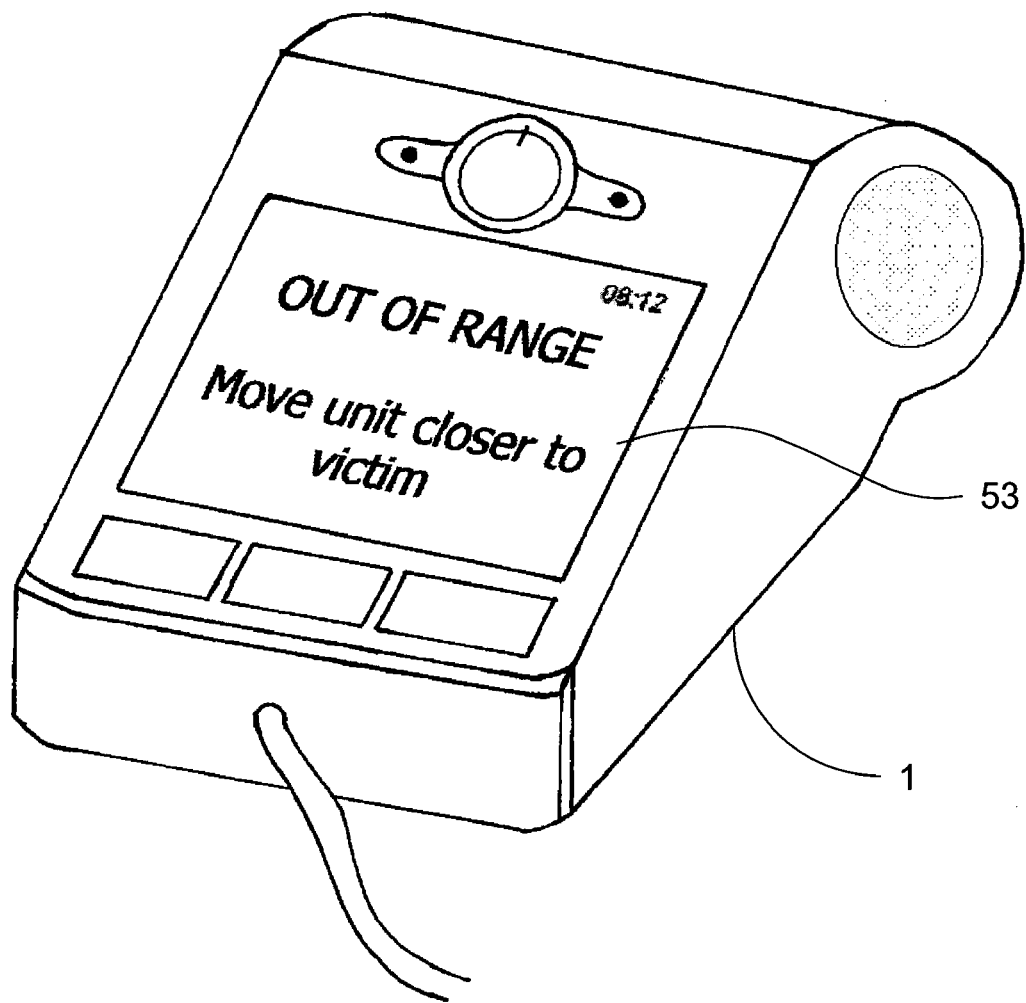
FIG. 32 is an illustration showing an example base unit displaying an example feedback prompt.

Beyond CPR related prompting, other information may be relayed to the user. For example, the system may be capable of detecting that the distance between the position sensor and the reference sensor is outside the operating range. In this scenario, the system may prompt 53 the user to move the base containing the reference sensor closer to the position sensor as shown in FIG. 32.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

The invention claimed is:

1. A system for determining a depth of compression of a chest of a patient receiving chest compressions, the system comprising:
  a field generator adapted to generate a field;
  a compound field detector including at least two coils at a fixed distance from each other, the field detector adapted to generate a response signal indicative of any one of the at least two coils detecting the field; and
  a processor adapted to determine from the response signal position information for the field detector relative to the field generator, and to determine the chest compression depth from the determined position information, the processor further adapted to receive signals from each of the coils, determine an apparent distance between the coils, and determine a correction factor to correct for distortion in the position information, the correction factor being determined based on any differences between the apparent distance and the fixed distance between the coils;
  wherein one of the field generator and the field detector is a position sensor adapted to move in accordance the chest as the chest is receiving the compressions, and the other of the field generator and the field detector is a reference sensor adapted to be stationary relative to the patient.

2. The system of claim 1 wherein the processor is further adapted to define initial positions for each of the coils at a given time, wherein the apparent distance is determined based on apparent distance traveled by one of the at least two coils from its own initial position to an initial position of another of the at least two coils.

3. A system for determining a depth of compression of a chest of a patient receiving chest compressions, the system comprising:
  a field generator adapted to generate a field;
  a compound field detector including at least two coils at a fixed distance from each other, the field detector adapted to generate a response signal indicative of any one of the at least two coils detecting the field; and
  a processor adapted to determine from the response signal position information for the field detector relative to the field generator, and to determine the chest compression depth from the determined position information;
    wherein the position information includes measured orientation angles of the position sensor;
  wherein one of the field generator and the field detector is a position sensor adapted to move in accordance the chest as the chest is receiving the compressions, and the other of the field generator and the field detector is a reference sensor adapted to be stationary relative to the patient.

4. The system of claim 3 wherein an angle of a direction of chest compression relative to an axis perpendicular to the patient's chest is calculated using the orientation angles.

5. A system for determining a depth of compression of a chest of a patient receiving chest compressions, the system comprising:
  a field generator adapted to generate a field;
  a compound field detector including at least two coils at a fixed distance from each other, the field detector adapted to generate a response signal indicative of any one of the at least two coils detecting the field; and
  a processor adapted to determine from the response signal position information for the field detector relative to the field generator, and to determine the chest compression depth from the determined position information;
  wherein one of the field generator and the field detector is a wearable position sensor adapted to move in accordance the chest as the chest is receiving the compressions, and the other of the field generator and the field detector is a reference sensor adapted to be stationary relative to the patient, and wherein a bend sensor is provided with the position sensor for sensing an orientation of the position sensor.

6. The system of claim 5 wherein measured data from the bend sensor is used to correct for noise and distortion from orientation information measured by the position sensor.

7. A system for determining a depth of compression of a chest of a patient receiving chest compressions, the system comprising:
  a field generator adapted to generate a field;
  a compound field detector including at least two coils at a fixed distance from each other, the field detector adapted to generate a response signal indicative of any one of the at least two coils detecting the field; and
  a processor adapted to determine from the response signal position information for the field detector relative to the field generator, and to determine the chest compression depth from the determined position information;
  wherein a distortion map of known distortions in an operating environment is stored in the processor, and the processor is further adapted to correct for the known distortions using the distortion map;

wherein one of the field generator and the field detector is a position sensor adapted to move in accordance the chest as the chest is receiving the compressions, and the other of the field generator and the field detector is a reference sensor adapted to be stationary relative to the patient.

8. The system of claim 7 wherein the processor is further adapted to detect the presence of known distortions in the environment and, in response to the detected presence, to automatically initiate use of the distortion map to correct for the known distortions.

9. The system of claim 7 wherein the distortion map is created by placing the field generator and field detector in the operating environment and determining electromagnetic fields at specific locations within the environment.

10. The system of claim 7 wherein the operating environment is inside an ambulance.

11. A system for determining a depth of compression of a chest of a patient receiving chest compressions, the system comprising:
a field generator adapted to generate a field;
a second field detector for taking into account any motion or displacement of a non-rigid surface supporting the patient;
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein one of the field generator and the field detector is a position sensor adapted to move in accordance the chest as the chest is receiving the compressions, and the other of the field generator and the field detector is a reference sensor adapted to be stationary relative to the patient.

12. The system of claim 11 wherein a first one of the compound field detector, the second field detector and the field generator is adapted to move in accordance with the non-rigid surface, a second one of the compound field detector, the second field detector and the field generator is adapted to move in accordance with the chest of the patient, and a third one of the compound field detector, the second field detector and the field generator is adapted to be stationary relative to the patient.

13. The system of claim 12 wherein motion or displacement of the non-rigid surface is taken into account by determining the relative motion between the first one of the compound field detector, the second field detector and the field generator adapted to move in accordance with the non-rigid surface, and the second one of the compound field detector, the second field detector and the field generator adapted to move in accordance with the chest of the patient.

14. A system for determining a depth of compression of a chest of a patient receiving chest compressions, the system comprising:
a field generator adapted to generate a field;
a force sensor
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein one of the field generator and the field detector is a position sensor with pressure sensor adapted to move in accordance the chest as the chest is receiving the compressions, and the other of the field generator and the field detector is a reference sensor adapted to be stationary relative to the patient;
wherein the processor is further adapted to correct for at least one of noise, distortion and hemisphere ambiguity in the position information using data from the force sensor.

15. The system of claim 14 wherein the processor is further adapted to determine chest recoil using data from the force sensor.

16. The system of claim 14 wherein the processor is further adapted to calculate a calibration constant for data from the force sensor using the position information.

17. The system of claim 16 wherein the calibration constant transforms the data from the force sensor into at least one of position data and depth data.

18. The system of claim 17 wherein the processor is further adapted to calculate the chest compression depth using the data from the force sensor in the absence of position information.

19. The system of claim 18 wherein the system receives power from a power source, and the processor is further adapted to turn off power to the field generator and use the data from the force sensor to conserve system power.

20. A system for determining a depth of compression of a chest of a patient receiving chest compressions, the system comprising:
a field generator adapted to generate a field;
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein one of the field generator and the field detector is a position sensor with pressure sensor adapted to move in accordance the chest as the chest is receiving the compressions, and the other of the field generator and the field detector is a reference sensor adapted to be stationary relative to the patient;
wherein the processor is further adapted to correct for at least one of noise, distortion and hemisphere ambiguity in the position information using data from the pressure sensor.

21. The system of claim 20 wherein the processor is further adapted to calculate a calibration constant for data from the pressure sensor using the position information.

22. The system of claim 21 wherein the calibration constant transforms the data from the pressure sensor into at least one of position data and depth data.

23. The system of claim 22 wherein the processor is further adapted to calculate the chest compression depth using the data from the pressure sensor in the absence of position information.

24. The system of claim 23 wherein the system receives power from a power source, and the processor is further adapted to turn off power to the field generator and use the data from the pressure sensor to conserve system power.

25. A system for determining a depth of compression of a chest of a patient receiving chest compressions, the system comprising:

a field generator adapted to generate a field;
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein one of the field generator and the field detector is a position sensor adapted to move in accordance the chest as the chest is receiving the compressions, and the other of the field generator and the field detector is a reference sensor with an accelerometer adapted to be stationary relative to the patient, wherein the accelerometer is adapted to detect movement of the reference sensor.

26. The system of claim 25 wherein movement detected by the accelerometer is used to correct for any movement of the reference sensor.

27. A system for determining a depth of compression of a chest of a patient receiving chest compressions, the system comprising:
a field generator adapted to generate a field;
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein the processor is further adapted to receive chest impedance data and to use the chest impedance data to correct for any noise and distortion in the position information;
wherein one of the field generator and the field detector is a position sensor adapted to move in accordance the chest as the chest is receiving the compressions, and the other of the field generator and the field detector is a reference sensor adapted to be stationary relative to the patient.

28. A system for determining a depth of compression of a chest of a patient receiving chest compressions, the system comprising:
a field generator adapted to generate a field;
a compound field detector including at least two coils at a fixed distance from each other, the field detector adapted to generate a response signal indicative of any one of the at least two coils detecting the field; and
a processor adapted to determine from the response signal position information for the field detector relative to the field generator, and to determine the chest compression depth from the determined position information;
wherein one of the field generator and the field detector is a position sensor adapted to move in accordance the chest as the chest is receiving the compressions, and the other of the field generator and the field detector is a reference sensor adapted to be stationary relative to the patient;
wherein the reference sensor and the processor are provided in a base unit, and the position sensor is in communication with the base unit.

29. The system of claim 28 wherein a power source is provided in the base unit, and an auxiliary power source is provided with the position sensor.

30. The system of claim 28 wherein the base unit comprises a feedback component for providing feedback to a CPR administrator based on at least one of the determined position information and the determined chest compression depth.

31. The system of claim 30 wherein the feedback comprises at least one of visual, audio, and tactile prompts.

32. A compound field detector for determining a depth of compression of a chest of a patient receiving chest compressions, the detector comprising:
at least two coils at a fixed distance from each other;
wherein the detector is adapted to generate a response signal indicative of any one of the at least two coils detecting a field;
wherein each coil comprises windings, and the windings of each coil are substantially parallel to the windings of each other coil; and
at least one perpendicular field detecting coil having windings perpendicular to and surrounding the at least two parallel coils.

33. The detector of claim 32 wherein the parallel coils share at least one common perpendicular coil.

* * * * *